(12) United States Patent
Chary

(10) Patent No.: US 9,394,515 B2
(45) Date of Patent: Jul. 19, 2016

(54) POULTRY PERFORMANCE

(71) Applicant: Zoetis Services LLC, Florham Park, NJ (US)

(72) Inventor: Parag Chary, Portage, MI (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 14/184,002

(22) Filed: Feb. 19, 2014

(65) Prior Publication Data

US 2014/0242569 A1 Aug. 28, 2014

Related U.S. Application Data

(60) Provisional application No. 61/767,961, filed on Feb. 22, 2013.

(51) Int. Cl.
| | |
|---|---|
| A61K 38/18 | (2006.01) |
| C12N 5/073 | (2010.01) |
| A61K 38/30 | (2006.01) |
| A23K 1/16 | (2006.01) |
| A23K 1/18 | (2006.01) |
| A61K 9/08 | (2006.01) |
| C07K 14/50 | (2006.01) |
| C07K 14/65 | (2006.01) |

(52) U.S. Cl.
CPC ............ *C12N 5/0604* (2013.01); *A23K 1/1631* (2013.01); *A23K 1/182* (2013.01); *A23K 1/1826* (2013.01); *A61K 9/08* (2013.01); *A61K 38/1825* (2013.01); *A61K 38/30* (2013.01); *C07K 14/50* (2013.01); *C07K 14/65* (2013.01)

(58) Field of Classification Search
None
See application file for complete search history.

(56) References Cited

U.S. PATENT DOCUMENTS

| | | | |
|---|---|---|---|
| 4,666,828 | A | 5/1987 | Gusella |
| 4,683,202 | A | 7/1987 | Mullis |
| 4,801,531 | A | 1/1989 | Frossard |
| 5,192,659 | A | 3/1993 | Simons |
| 5,272,057 | A | 12/1993 | Smulson et al. |
| 5,916,869 | A | 6/1999 | Croom, Jr. et al. |
| 2002/0127234 | A1 | 9/2002 | El Halawani et al. |

FOREIGN PATENT DOCUMENTS

| | | |
|---|---|---|
| WO | WO 94/06445 | 3/1994 |
| WO | WO 2005/047334 A1 | 5/2005 |

OTHER PUBLICATIONS

Kuang, S. and Rudnicki, M. A., 2008, "The emerging biology of satellite cells and their therapeutic potential," Trends in Molecular Medicine, vol. 14(2), pp. 82-91.
Pearson, W. R., 1990, "Rapid and Sensitive Sequence comparison with FASTP and FASTA," Methods in Enzymology, vol. 183, pp. 63-98.
Pearson, W. R., 2000, "Flexible sequence similarity searching with the FASTA3 program package," Methods in Molecular Biology, vol. 132, 185-219, here listed 1-32 downloaded from website http://people.virginia.edu/~wrp/pearson.html, print out date, Apr. 28, 2014.
Altschul, S. F. et al., 1990, "Basic Local Alignment Search Tool," Journal of Molecular Biology, vol. 215, pp. 403-410.
Altschul, S. F. et al., 1997, "Gapped BLAST and PSI-BLAST: a new generation of protein database search programs," Nucleic Acids Research, vol. 25, pp. 3389-3402.
Henry, M. H. and Burke, W. H., 1999, "The Effects of In Ovo Administration of Testosterone or an Antiandrogen on Growth of chick Embryos and Embryonic Muscle Characteristics," Poultry Science, vol. 78, pp. 1006-1013.
Keralapurath, M. M. et al., 2010, "Effects of in ovo injection of L-carnitine on hatchability and subsequent broiler performance and slaughter yield," Poultry Science, vol. 89, pp. 1497-1501.
Wilson, H. R. et al., 1983, "Abdominal Fat Pad Reduction in Broilers with Thyroactive Iodinated Casein," Poultry Science, vol. 62, pp. 811-818.
Vasilatos-Younken, R., 1999, "Absence of Growth Hormone-Induced Avian Muscle Growth In Vivo," Poultry Science, vol. 78, pp. 759-768.
Huybrechts, L. M. et al., 1992, "Effect of Recombinant Human Insulin-Like Growth Factor-I on Weight Gain, Fat Content, and Hormonal Parameters in Broiler Chickens," Poultry Science, vol. 71, pp. 181-187.
Tixier-Boichard, M. et al., 1992 "Effects of insulin-like growth factor-I (IGF-I) infusion and dietary tri-iodothyronine ($T_3$) supplementation on growth, body composition and plasma hormone levels in sex-linked dwarf mutant and normal chickens," Journal of Endocrinology: vol. 133, pp. 101-110.
Spencer, G. S. G. et al., 1990 "Lack of effect of exogenous insulin-like growth factor-I (IGF-I) on chick embryo growth rate," Reproduction, Nutrition, Development; vol. 30(4), pp. 515-521.
Kocamis, H. et al., 1998, "In Ovo Administration of Recombinant Human Insulin-Like Growth Factor-I Alters Postnatal Growth and Development of the Broiler Chicken", Poultry Science, vol. 77, pp. 1913-1919.
Halevy, O. et al., 2006. "Enhancement of meat production by environmental manipulations in embry and young broilers", World's Poultry Science Journal, vol. 62, pp. 485-497.

*Primary Examiner* — Marianne P Allen
(74) *Attorney, Agent, or Firm* — Kelly M. Sullivan

(57) ABSTRACT

Methods for increasing breast muscle weight in poultry are disclosed herein. These methods can include delivery of compositions via in ovo administration. The methods disclosed herein also encompass the delivery of proteins. The methods disclosed herein are effective for increasing breast muscle weight in poultry, both in the embryo, and at slaughter age.

6 Claims, 12 Drawing Sheets

Summary of Average Day 35 Breast Weight for Males

Summary of Average Day 35 Breast Weight for Females

POULTRY PERFORMANCE

CROSS REFERENCE TO RELATED APPLICATIONS

This application claims priority from U.S. Provisional Application No. 61/767,961 filed Feb. 22, 2013 which is herein incorporated by reference in its entirety.

FIELD OF THE INVENTION

The subject of the present application is a method of improving performance in poultry via delivery of substrates to the egg prior to hatching. This results in an increase in muscle growth and weight, both pre- and post-hatch.

BACKGROUND

Currently there exists a need to improve the growth performance of poultry, which includes increasing the rate of formation and amount of muscle, as well as a corresponding increase in muscle weight. Due to the expanding emphasis on identifying eco-friendly approaches to achieve performance improvements in poultry and other food animals, it is desirable that such strategies not involve the use of steroids or other chemical hormones.

In poultry, satellite cells are considered to be the progenitors of muscle cells. Under physiological conditions in which satellite cells are activated, they proliferate, and undergo differentiation into mature muscle cells (reviewed in Kaung and Rudnicki, Trends in Mol Med; 14(2):82-91; 2008). There are essentially two stages during which poultry satellite cells can be targeted for proliferation and differentiation—the pre-hatch (embryonic) stage, and post-hatch. Thus, there exists an unmet need to identify a suitable composition, as well as to identify the correct timing and administration route for that composition, to achieve an increase in muscle weight in poultry.

SUMMARY OF THE INVENTION

The method of the present invention surprisingly and unexpectedly provides examples that demonstrate that the administration of proteins in ovo leads to a significant increase in muscle weight during both the pre-hatch and post-hatch stages.

In one embodiment of the present invention provides a method of increasing muscle weight in an avian, comprising administration of a composition comprising a protein in ovo. In one or more embodiments of the invention provides that the protein is selected from the group consisting of a fibroblast growth factor and insulin-like growth factor. In one or more embodiments the protein is Fibroblast Growth Factor. In one embodiment, the protein is Fibroblast Growth Factor-2 (FGF-2). In one embodiment, the protein is Insulin-like Growth Factor. In one embodiment the protein is Insulin-like Growth Factor-1. In one embodiment of the invention provides that the protein is selected from the group consisting of a Fibroblast Growth Factor-2 (FGF-2) and Insulin-like Growth Factor-1 (IGF-1) or variants thereof.

In one or more embodiments of the present invention provides the protein is selected from the group consisting of SEQ ID NO. 1-4 or variants thereof. In one or more embodiments of the present invention provides that the protein is SEQ ID NO. 1, or a variant thereof. In one or more embodiments of the present invention provides that the protein is SEQ ID NO. 2, or a variant thereof. In one or more embodiments of the present invention provides that the protein is SEQ ID NO. 3, or a variant thereof. In one or more embodiments of the present invention provides that the protein is SEQ ID NO. 4, or a variant thereof. In one or more embodiments the peptide is a recombinant protein.

In one or more embodiments of the present invention the method provides that the dose of Fibroblast Growth Factor-2 administered in ovo is up to about 120 ng/egg. In one or more embodiment the dose of FGF-2 is about between 10 ng/egg and 60 ng/egg. In one of more embodiments of the present invention the method provides that the dose of Insulin-like Growth Factor-1 is up to about 200 ng/egg.

In one or more embodiments of the present invention the method provides that the avian is selected from the group consisting of: chicken; turkey; guinea fowl; pheasant; quail; peacock; duck; goose; pigeons; doves, and ratites. In one embodiment the avian comprises a chicken.

In one embodiment of the present invention, the method provides that administration of the composition of the invention is by in ovo injection. In one embodiment the in ovo injection is performed by a device that pierces the egg shell and delivers the treatment substance to the interior of the egg. In one embodiment, the method provides that the method of administration is by manual in ovo vaccination.

In one or more embodiments the method of the invention is administered between about embryonal day 0 and 18. In one embodiment the administration occurs between about embryonal day 0 and day 4. In one or more embodiments, the administration occurs about on embryonal day 0. In one or more embodiments, the administration occurs about on embryonal day 1. In one or more embodiments, the administration occurs about on embryonal day 2. In one or more embodiments the administration occurs about on embryonal day 3. In one embodiment the administration occurs on about embryonal day 4. In one or more embodiments the administration of the composition of the invention occurs between about embryonal day 4 and embryonal day 18. In one embodiment, the administration of the composition of the invention occurs in the last quarter of embryonic development. In one or more embodiments, the administration of the composition occurs about on embryonal day 18.

In one embodiment, the protein has an extended half life. In one or more embodiments the protein is chemically modified. In one or more embodiments the protein is a fusion protein. In one embodiment the fusion protein comprises an Fc fragment.

In one embodiment of the present invention the administration of said protein leads to an increase of at least about 2% of muscle weight. In one embodiment the administration of the protein leads to between about 2% to 10% in muscle weight at slaughter age. In one or more embodiments, the method of the invention provides that the in ovo administration of the protein of the invention leads to an increase in muscle weight between about 3-7%. In one embodiment of the present method leads to an increase in satellite cell proliferation. In one embodiment, the increase in satellite cell proliferation leads to an increase in muscle hyperplasia.

In one or more embodiments of the present invention, the method provides a use of a composition comprising a protein for increasing muscle growth in poultry, comprising administration by the method the present invention.

In one embodiment the invention provides a method of determining increased growth in avians by measuring the levels of transcripts of proteins such as MyoD, Myogenin, Syndecan and Glypican-1 in breast muscle tissues by measuring RNA levels.

DESCRIPTION OF THE SEQUENCES

Figure 1A:
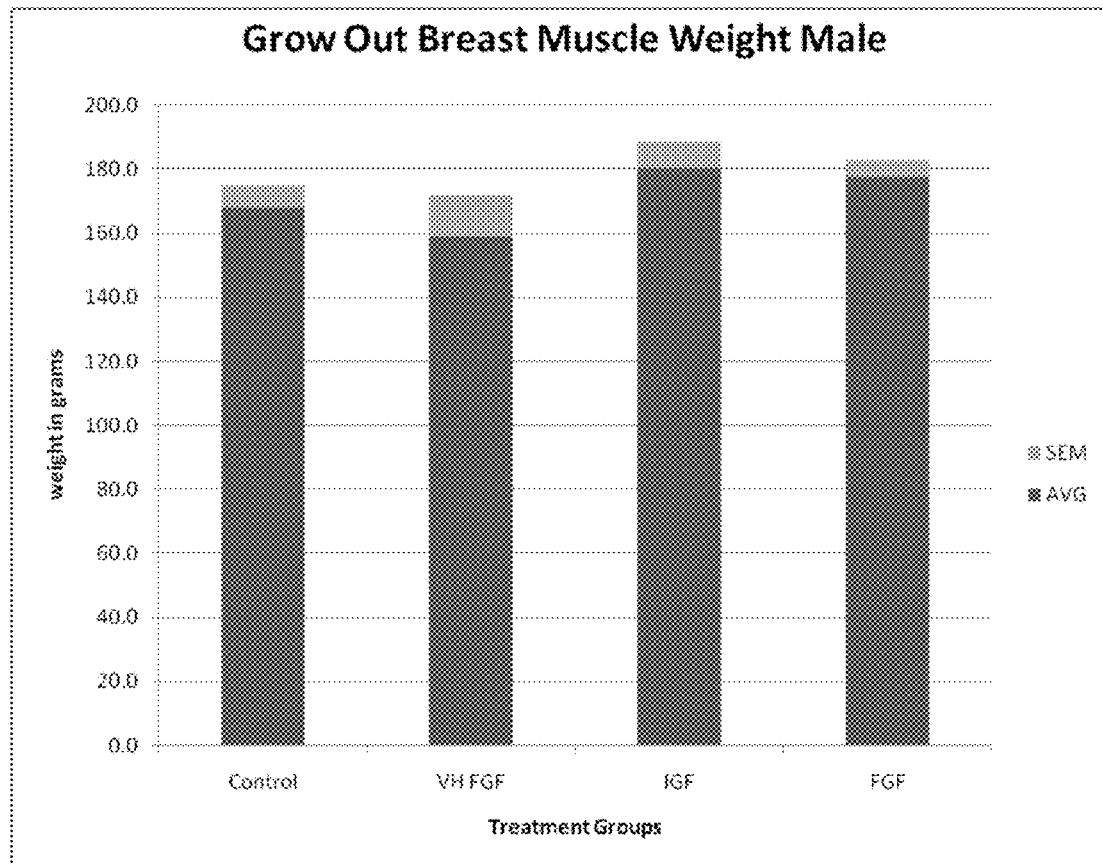
FIGS. 1A and B: Graphical representation of a summary of average Day 35 (grow out) breast muscle weight for males (A) and females (B) after ED4 in ovo injection with 120 ng FGF-2 (VH), 200 ng IGF-1 and 40 ng FGF-2 as compared to in ovo injection with PBS (control)
Figure 1B:
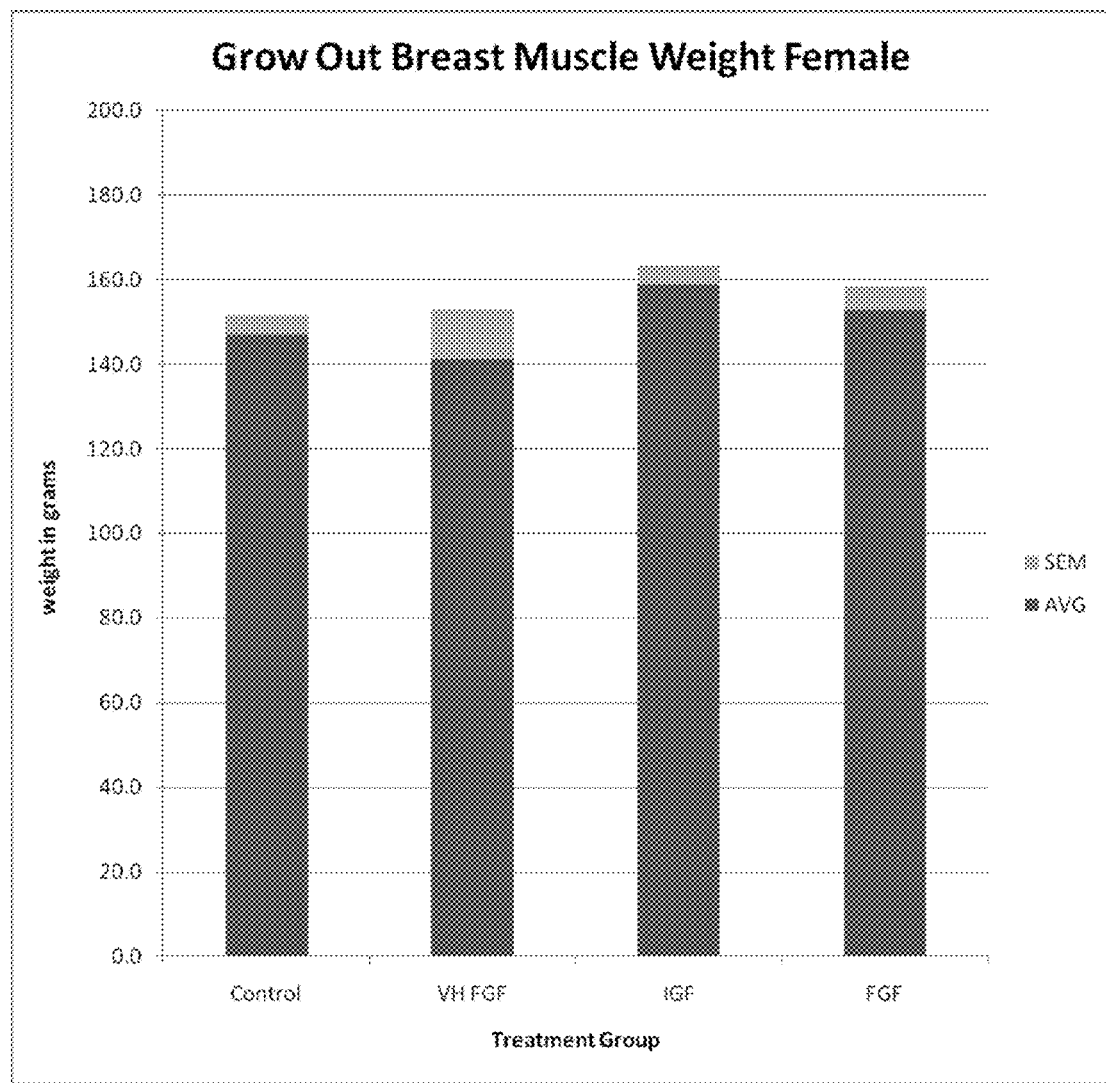
Figure 2A:
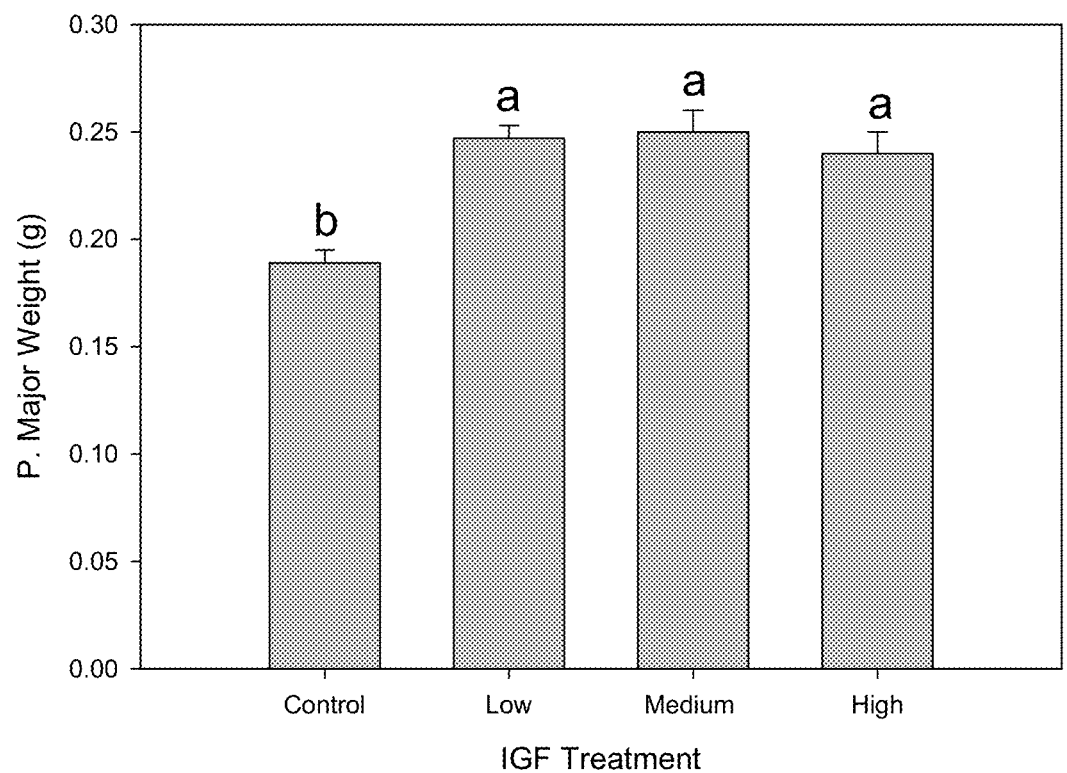
FIG. 2A: Graphical representation of measurements of major weight of Pectoralis major muscle as measured on embryonal day 18 (ED18) after ED4 in ovo treatment with 50 ng IGF-1 (low), 100 ng IGF-1 (medium) and 200 ng IGF-1 (high) and PBS (control).
Figure 2B:
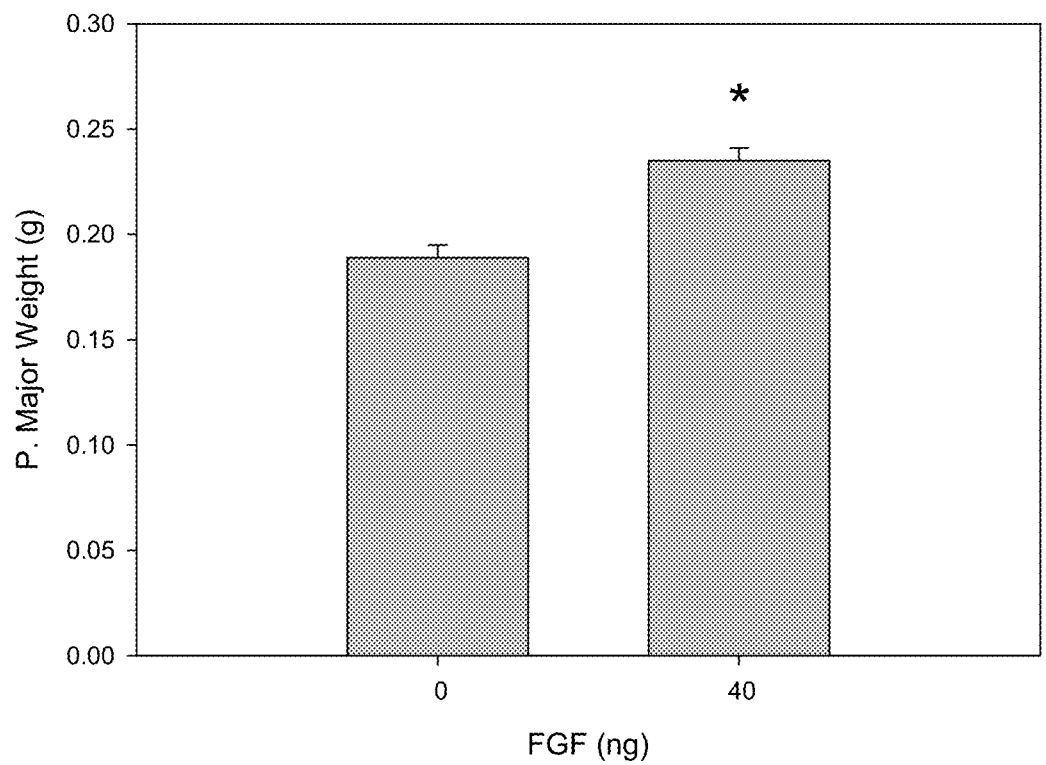
FIG. 2B: Graphical representation of measurements of major weight of Pectoralis major muscle as measured on embryonal day 18 (ED18) after ED4 in ovo treatment with 40 ng FGF-2 and PBS (control).
Figure 3A:
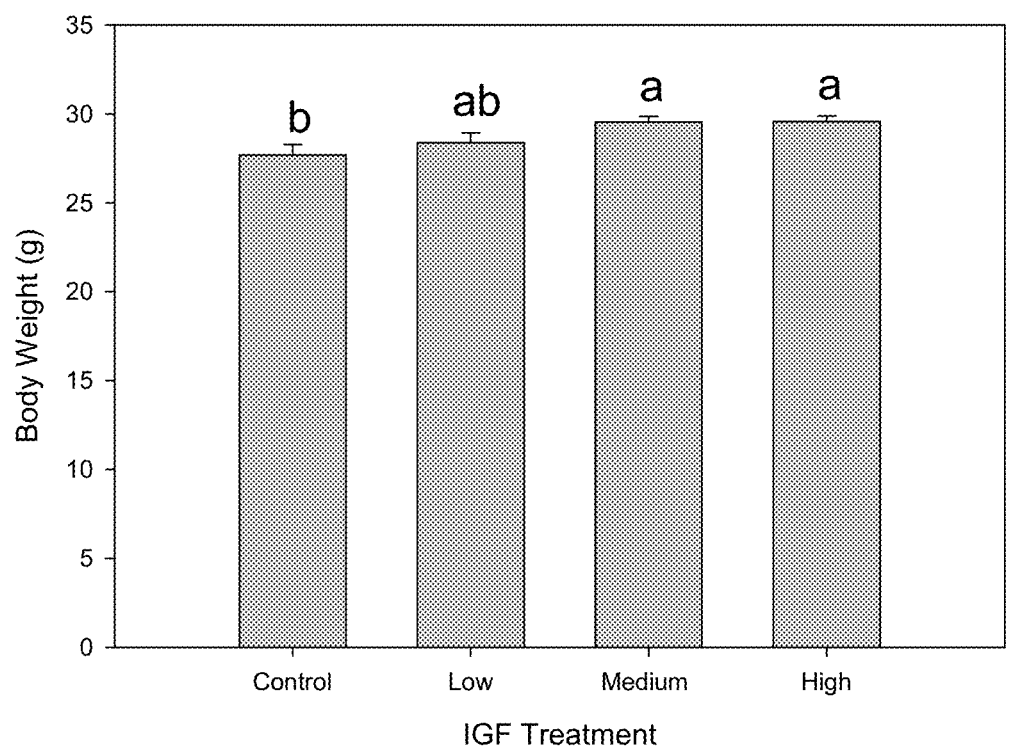
FIG. 3A: Graphical representation of body weight at embryonal day 18 (ED18) after ED4 in ovo treatment with 50 ng IGF-1 (low), 100 ng IGF-1 (medium) and 200 ng IGF-1 (high) and PBS (control).
Figure 3B:
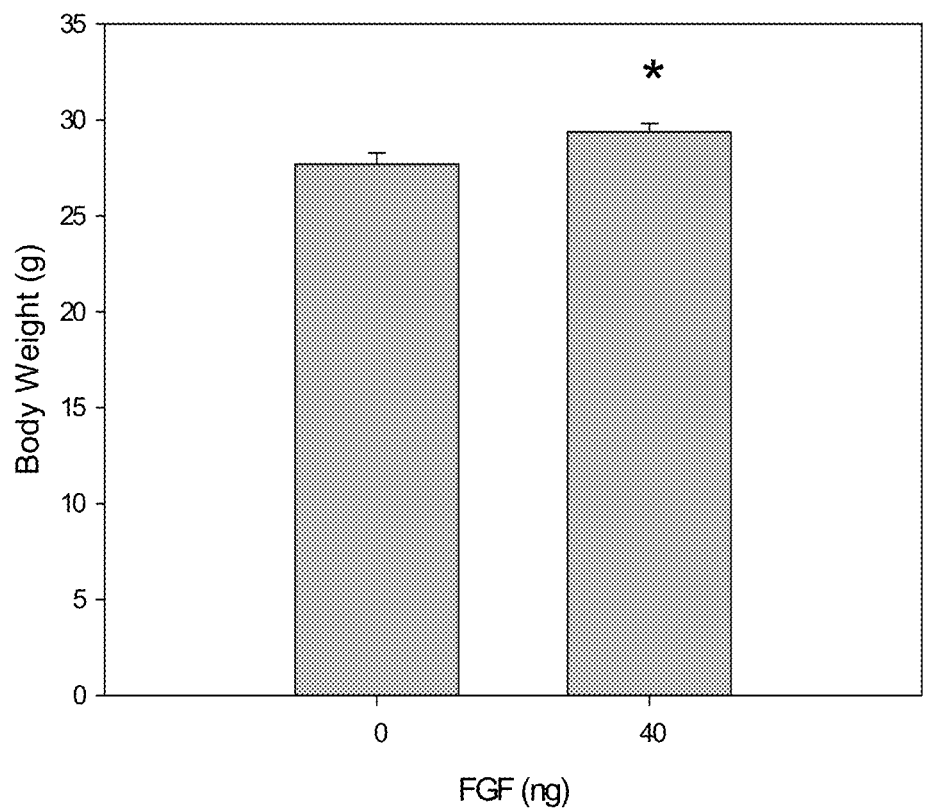
FIG. 3B: Graphical representation of body weight at embryonal day 18 (ED18) after ED4 in ovo treatment with 40 ng FGF-2 and PBS (control).
Figure 4A:
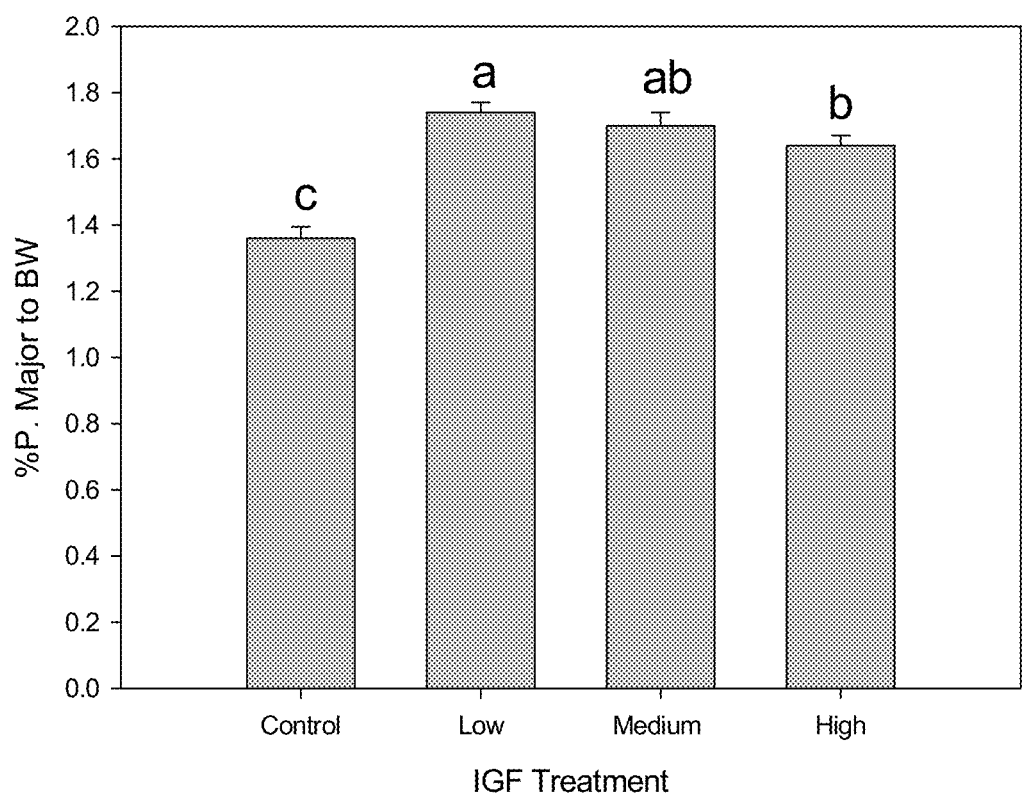
FIG. 4A: Graphical representation of Pectoralis major as a percentage of body weight at embryonal day 18 (ED18) after ED4 in ovo treatment with 50 ng IGF-1 (low), 100 ng IGF-1 (medium) and 200 ng IGF-1 (high) and PBS (control).
Figure 4B:
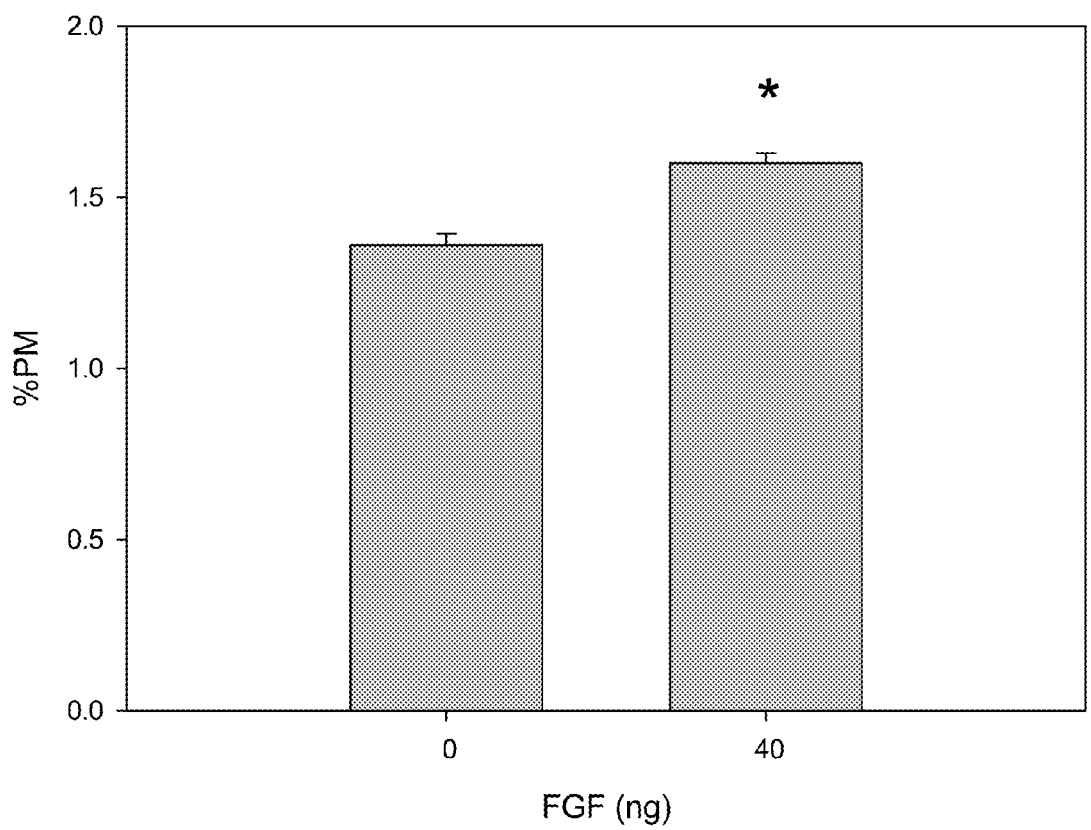
FIG. 4B: Graphical representation of Pectoralis major as a percentage of body weight at embryonal day 18 (ED18) after ED4 in ovo treatment with 40 ng FGF-2 and PBS (control).

| | |
|---|---|
| SEQ ID NO: 1: | Amino acid sequence of the mature form of human FGF 2. |
| SEQ ID NO: 2: | Amino acid sequence of the mature form of human IGF 1. |
| SEQ ID NO: 3: | Amino acid sequence of the mature form of chicken FGF 2. |
| SEQ ID NO: 4: | Amino acid sequence of the mature form of chicken IGF 1. |
| SEQ ID NO: 5: | Nucleic acid sequence for turkey MyoD forward primer. |
| SEQ ID NO: 6: | Nucleic acid sequence for turkey MyoD reverse primer. |
| SEQ ID NO: 7: | Nucleic acid sequence for turkey Myogenin forward primer. |
| SEQ ID NO: 8: | Nucleic acid sequence for turkey Myogenin reverse primer. |
| SEQ ID NO: 9: | Nucleic acid sequence for glypican1 forward primer. |
| SEQ ID NO: 10: | Nucleic acid sequence for glypican1 reverse primer. |
| SEQ ID NO: 11: | Nucleic acid sequence for syndecan4 forward primer. |
| SEQ ID NO: 12: | Nucleic acid sequence for syndecan4 reverse primer. |

DETAILED DESCRIPTION

All publications, patent applications, patents, and other references mentioned herein are incorporated by reference in their entirety.

The following definitions may be applied to terms employed in the description of the embodiments. The following definitions supercede any contradictory definitions contained in each individual reference incorporated herein by reference.

The terminology used in the description of the invention herein is for the purpose of describing particular embodiments only and is not intended to be limiting of the invention.

As used in the description of the invention and in the claims, the singular forms "a", "an" and "the" are intended to include the plural forms as well, unless the context clearly indicates otherwise.

The terms "about" or "approximately" as used herein, unless otherwise indicated, when used in connection with a measurable numerical variable, mean the indicated value of the variable, and all values of the variable that are within the experimental error of the indicated value (e.g., within the 95% confidence interval for the mean), or within 10 percent of the indicated value, whichever is greater.

The term "air cell", as used herein, unless otherwise indicated, means the empty space between the white and shell at the large end of an egg.

The term "amino acid", as used herein, unless otherwise indicated, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example but not limited to, hydroxyproline, carboxyglutamate, and O-phosphoserine. Stereoisomers (e.g., D-amino acids) of the twenty conventional amino acids, unnatural amino acids such as α and α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids.

Amino acid analogs refer to compounds that have the same basic chemical structure as a naturally occurring amino acid, i.e., a carbon that is bound to a hydrogen, a carboxyl group, an amino group, and an R group. Exemplary amino acid analogs include, for example, homoserine, norleucine, methionine sulfoxide, and methionine methyl sulfonium. Such analogs have modified R groups (e.g., norleucine) or modified peptide backbones, but retain the same essential chemical structure as a naturally occurring amino acid. Amino acid mimetics refer to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission.

The term "avian" is intended to include males or females of any avian species, but is primarily intended to encompass poultry which are commercially raised for eggs or meat. Accordingly, the term "avian" is particularly intended to encompass hens, cocks and drakes of chickens, turkeys, ducks, geese, quail and pheasant.

The term "embryo" as used herein, unless otherwise indicated, means the multi-cellular diploid eukaryote within a fertilized egg. The terms "embryonal day" or "ED" as used herein, unless otherwise indicated, means the number of days since a fertilized egg was put in an incubator. It is known to those of skill in the art that upon laying of a fertilized avian egg, the egg will begin developing in ovo after being placed in an incubator at the appropriate incubating temperature. ED0 is thus defined as the day that the egg is placed in the incubator post-lay; ED21 is generally considered to be the day of hatch for a chicken embryo. The term "early embryonic stage" as used herein, is being used to describe the earliest embryonic stages beginning with ED0 and ending with the end of ED4. The term "later embryonic stage", as used herein, is being used to describe the last quarter of incubation of the embryo. This stage can be defined as about around ED18 (embryonic day 18).

The term "final quarter of incubation", as used herein, unless otherwise indicated, means the final quarter of incubation of a developing egg of a bird or a domesticated bird. In some embodiments the final quarter of incubation refers to, in the case of chickens, in ovo administration preferably done on days 15-20 of incubation, and most preferably on days 18 or 19 of incubation. In the case of turkeys, in ovo administration is preferably done on days 21-26 of incubation.

The term "fusion protein", as used herein, means a fusion protein, in particular Fc fusion proteins, that are created through the joining of two or more genes which originally coded for separate proteins. Translation of this fusion gene results in a single polypeptide with functional properties derived from each of the original proteins. Recombinant fusion proteins are created artificially by recombinant DNA technology for use in biological research or therapeutics. Fc-based fusion proteins, are where the Fc domain of an antibody of the IgG isotype is joined to a different protein.

The term "half-life" as used herein, unless otherwise indicated, means the time it takes for half the amount of a protein to be either degraded, disappear, or be removed from a population.

The terms "fibroblast growth factor", "fibroblast growth factor-1" or "FGF-1", "fibroblast growth factor-2", or "FGF-2" as used herein, unless otherwise indicated, mean a protein which is a member of a family of growth factors involved in angiogenesis, wound healing and embryonic development. The Fibroblast Growth Factors (FGFs) are heparin-binding proteins and interactions with cell-surface-associated heparin sulfate proteoglycans and have been shown to be essential for FGF signal transduction. The functions of FGFs in developmental processes may include mesoderm induction, antero-posterior patterning, limb development, neural induction and neural development, and in mature tissues/systems angiogenesis, keratinocyte organization, and wound healing processes.

The term "glypican" or "glypican-1", as used herein, unless otherwise indicated, means a protein in a family of proteins considered to be heparin sulfate proteoglycans. Glypicans can modify cell signaling pathways and contribute to cellular proliferation and tissue growth. Increased expression of glypican-1 suggests increased tissue growth.

The term "grow-out" as used herein, unless otherwise indicated, means the period of time between hatch and harvesting of a bird for consumption. The term "immediately after hatch" is known in the relevant field to refer to Day 0 in grow-out. The term "slaughter age" as used herein, unless otherwise indicated, means the day on which a bird is harvested.

The term "in ovo administration", or "in ovo injection" as used herein, unless otherwise indicated, means injection of the composition of the invention into an avian egg containing an embryo, as described herein, by any means of penetrating the shell of the egg and introducing the composition. The in ovo route of administration provides a convenient method of delivering a uniform dose of composition to each embryo while it is still in the egg. The term in ovo administration can refer to a number of different administration procedures all used to inject the composition of the invention into an avian egg. As is well known to one skilled in the art in ovo injections can be done in a variety of ways using different techniques and volumes of reagents. In essence, in ovo injection can be defined as the delivery process using a device or using manual techniques that pierce the egg shell and deliver the treatment substance to the interior of the egg. This administration can be a manual procedure, for example, where the air cell, or any other structure inside of each egg is located by candling and marked in pencil. By way of definition, candling is a method used in to study or locate the areas of growth and development of an embryo inside an egg. The method uses a bright light source behind the egg to show details through the shell, and is so called because the original sources of light used were candles. A hole is punched in the center of the area marked by the circle using a needle whereby the assigned treatment is administered in a small yet variable volume by dropping the composition of the invention into the punched hole. The hole is then sealed with glue and the egg is placed in the incubator. Additionally, in ovo administration can mean a method performed by any device that pierces the egg shell and delivers the treatment substance to the interior of the egg. The method of the present invention is not limited by the method of in ovo injection. The injection may be performed manually. The injection may be performed by a device. Additionally the method of the invention is not limited by location of injection into the egg. For example, in ovo injections performed at earlier embryonic stages may be but are not limited to being administered into the air cell of the egg. In ovo injections performed at later embryonic stages, for example at or about embryonic day 18 (ED 18), may be but are not limited to being administered into the amnion of the egg.

The terms "insulin-like growth factor", "Insulin-like Growth Factor-1", or "IGF-1" as used herein, unless otherwise indicated, mean a protein having high sequence similarity to insulin. IGF's are part of a complex system of cells used to communicate with their physiologic environment. IGF-1 consists of 70 amino acids in a single chain with three intramolecular disulfide bridges. IGF-1 has a molecular weight of 17,066 daltons. Its primary action is mediated by binding to its specific receptor, the Insulin-like growth factor 1 receptor, abbreviated as "IGF1R" present on many cell types in many tissues. Binding to the IGF1R, a receptor tyrosine kinase, initiates intracellular signaling; IGF-1 is one of the most potent natural activators of the AKT signaling pathway, a stimulator of cell growth and proliferation, and a potent inhibitor of programmed cell death. IGF-1 is a primary mediator of the effects of growth hormone (GH). Insulin-like Growth Factor 1 receptor (IGF-1R) and other tyrosine kinase growth factor receptors signal through multiple pathways.

The terms "muscle mass" or "muscle growth" as used herein, unless otherwise indicated, mean an increase in muscle weight. This can be separated into two periods, hyperplasia and hypertrophy. The term "hyperplasia", as used herein, is considered to be a physiological (normal) response to a specific stimulus, and the cells of a hyperplastic growth remain subject to normal regulatory control mechanisms. In the scope of the present invention hyperplasia is defined as an increase in the number of muscle cells or fibers. The term "hypertrophy" is the increase in the volume of a tissue due to the enlargement of its component cells. Hypertrophy should be distinguished from hyperplasia where the cells remain approximately the same size but increase in number.

The method of the present invention has surprisingly and unexpectedly shown a hyperplastic response, or increase in actual muscle number. This is compared to what has been observed versus hypertrophic muscle volume increase. Hyperplasia allows for a parallel increase in blood supply as compared to hypertrophy which does not allow for a parallel increase in blood supply. Thus far the poultry industry has been focused on quick gains through the hypertrophy process which has lead to poor vascular supply in market age birds with problems of muscle necrosis. The method of the present invention has surprisingly and unpredictably shown unprecedented levels of hyperplasia based on good vascular supply to the muscle which has done away with the problem of muscle necrosis issues.

The term "Myogenin" as used herein, is a muscle specific transcription factor involved in the coordination of skeletal muscle development and repair. An increased amount of myogenin present suggests an increase in skeletal muscle development.

The term "MyoD", as used herein, is defined as a protein with a key role in regulating muscle differentiation. MyoD belongs to a family of proteins known as myogenic regulatory factors. These basic helix loop helix transcription factors act sequentially in myogenic differentiation. MyoD is one of the earliest markers of myogenic commitment. MyoD is expressed in activated satellite cells, but not in quiescent satellite cells.

The term "polypeptide", "peptide", "protein" or the like as is well known and used interchangeably in the art and refers to a polymer of amino acids linearly linked by amide bonds (also known as peptide bonds) without regard to the length of the polymer. Thus, peptides, dipeptides, tripeptides, oligopeptides, and proteins are included within the definition of polypeptide. This term also does not specify or exclude post-expression modifications of polypeptides, for example but are not limited to polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

"Pharmaceutically acceptable", as used herein, unless otherwise indicated, refers to substances which are, suitable for use in contact with the tissues of subjects without undue toxicity, irritation, allergic response, and the like, commensurate with a reasonable benefit-to-risk ratio and effective for their intended use.

The terms "polynucleotide" or "polynucleotide molecule", as used herein, unless otherwise indicated, mean an organic polymer molecule composed of nucleotide monomers covalently bonded in a chain. DNA (deoxyribonucleic acid) and RNA (ribonucleic acid) are examples of polynucleotides with distinct biological function.

The term "poultry" as used herein, unless otherwise indicated, means domesticated fowl kept primarily for meat and eggs. The term includes birds of the order Galliforme, e.g. the chicken, turkey, guinea fowl, pheasant, quail, and peacock; and Anserigormes (swimming birds) e.g. the duck and goose. The term also refers to pigeons, doves, and ratites (including, but not limited to, ostriches). The terms "poultry", "bird", and "avian" are herein used interchangeably.

With respect to chickens, they can be divided into two main groups—those reared for laying eggs ("layers"), and those reared for meat production ("broilers"). Broilers are the preferred target of the methods of the disclosed invention. Broilers are specifically bred for large-scale, efficient meat production, and generally grow much faster than egg-laying hens or traditional dual purpose breeds. They have very fast growth rates, a high feed conversation rate, and exhibit a relatively low level of activity. They often can reach a slaughter weight of 4-5 pounds (dressed) in only 5 weeks. This period of time is termed the "grow-out" period. Regarding breeds of chickens, the methods of the present invention have applicability to all breeds. There are many different breeds of commercial birds. The more popular broiler breeds are, but are not limited to, the Cobb and Ross breeds. Cobb is an American variety of the French Pullet de Breese breed, and came into existence in the late 1980's. Cobb birds typically have a grow-out period of 35 days (5 weeks). The Ross breed is from New Zealand, and resulted from a cross between a Scottish Ross and American Cobb. Ross birds typically have a grow-out period of 42 days (6 weeks). The method of the present invention is not limited by the breed of the bird being treated however, and the eggs of any breed, commercial or otherwise, can be used.

One embodiment of the present invention is a method providing in ovo administration of compositions comprising proteins. The growth cycle in ovo of a chicken embryo is approximately 21 days. At any time during this 21 day cycle, the methods of the present invention could be carried out. The methods of the present invention could be carried on or about between 0 (embryonal day 0, or ED0), the last quarter of incubation or on or about ED18 (embryonal day 18) days of incubation. The methods of the present invention could also be carried out at on or about between ED0 and ED4, or on or about ED0, or on or about ED4.

The terms "recombinant protein" or "recombinant" as used herein, unless otherwise indicated, mean proteins, peptides or polypeptides derived, and the techniques well known to one of skill in the art and are used to produce them, from cells transformed by an exogenous DNA construct encoding the desired protein, peptide or polypeptide.

The term "satellite cells", as used herein are precursors to skeletal muscle cells, or precursor cells and are able to give rise to satellite cells or differentiated skeletal muscle cells. They have the potential to generate new muscle fibers, provide additional myonuclei to their parent muscle fiber, or return to a quiescent state. More specifically, upon activation, satellite cells can re-enter the cell cycle to proliferate and differentiate into myoblasts.

The term "slaughter age" as used herein, unless otherwise indicated, means the age at which a poultry species is killed for consumption.

The term "Syndecan", as used herein, are single transmembrane domain proteins that are thought to act as coreceptors, especially for G protein-coupled receptors. These core proteins carry three to five heparan sulfate and chondroitin sulfate chains, which allow for interaction with a large variety of ligands including fibroblast growth factors, vascular endothelial growth factor, transforming growth factor-beta, fibronectin and antithrombin-1.

The term "therapeutically effective amount" as used herein, unless otherwise indicated, means the amount necessary to bring about a desired positive effect. In the case of muscle, a therapeutically effective amount would be that necessary to show a demonstrable increase in muscle weight.

The term "variant", as used herein, are peptides that are defined as in reference to a specific polypeptide that encompasses polypeptides that are more than 70%, more than 80%, more than 85%, more than 90%, more than 95%, or more than 97%, or more than 98% identical in amino acid sequence to the original polypeptide, but without essentially detracting from the properties thereof. Such variants, for example, can be the result of natural variation or genetic engineering, including deletions, insertions, and/or substitutions.

The amino acid sequence identity of polypeptides can be determined conventionally using known computer programs such as Bestfit, FASTA, or BLAST (see, e.g. Pearson, *Methods Enzymol.* 183:63-98 (1990); Pearson, *Methods Mol. Biol.* 132:185-219 (2000); Altschul et al., *J. Mol. Biol.* 215:403-410 (1990); Altschul et al., *Nucleic Acids Res.* 25:3389-3402 (1997)). When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, fragments, or variants thereof disclosed herein.

The term "veterinarily-acceptable carrier", or "carrier" as used herein, unless otherwise indicated, means substances which are, within the scope of sound medical judgment, suitable for use in contact with the tissues of animals without undue toxicity, irritation, allergic response, and the like, commensurate with a reasonable benefit-to-risk ratio, and effective for their intended use.

The following description is provided to aid those skilled in the art in practicing the present embodiments of the invention. Even so, this description should not be construed to unduly limit the present invention as modifications and variations in the embodiments discussed herein can be made by those of ordinary skill in the art without departing from the spirit or scope of the present inventive discovery.

Currently there exists a need to improve the growth performance of poultry, which includes increasing the rate of formation and amount of muscle, as well as a corresponding increase in muscle weight. The method of the present invention has shown a hyperplastic response, or an increase in actual muscle. Hyperplasia allows for a parallel increase in blood supply as compared to hypertrophy which does not allow for a parallel increase in blood supply. Thus far the poultry industry has been focused on quick gains through the hypertrophy process which has lead to poor vascular supply in market age birds with problems of muscle necrosis. The method of the present invention has surprisingly and unpredictably shown unprecedented levels of hyperplasia and based on good vascular supply to the muscle has done away with the problem of muscle necrosis issues.

As previously defined satellite cells are a skeletal muscle-specific heterogeneous stem or progenitor cell. They are characterized by sublaminar localization, myogenic potential, and self-renewal capability. Under physiological conditions in which satellite cells are activated, they proliferate, and undergo differentiation into mature muscle cells (reviewed in Kaung and Rudnicki, Trends in Mol Med; 14(2):82-91; 2008). Many previous studies have attempted to show a stimulation of satellite cells which would result in increased muscle weight, therefore considered improved performance. For example: administration of steroids, either pre- or post-hatch, did not lead to satellite cell stimulation and subsequent increase in muscle mass. Henry and Burke (Poultry Sci.; 78:1006-1013, 1999) did not see a positive effect on breast weight when testosterone was administered in ovo. Keralapurath et al. (Poultry Sci.; 89:1497-1501, 2010) did not see an increase in performance or slaughter yield when L-carnitine was administered in ovo. In addition, the use of steroids is generally not considered to be an environmentally-friendly means of treating animals which will enter the human food chain.

Wilson et al. (Poultry Sci.; 62:811-815, 1983) did not see an increase in breast weight when thyroactive iodinated casein was delivered post-hatch. Vasilatos-Younken (Poultry Sci; 78:759-768, 1999) did not see induction of avian muscle growth when growth hormone was administered post-hatch. Neither Huybrechts et al. (Poultry Sci; 71:181-187, 1992), nor Tixier-Boichard et al. (J Endocrinol; 133:101-110, 1992), saw an increase in weight gain when insulin-like growth factor-1 (IGF-1) was administered post-hatch. Spencer et al. (Reproduction, Nutrition, Development; 30(4):515-521, 1990), when administering IGF-1 in ovo, did not see a significant positive impact on total body weight and other parameters, and concluded that administration of exogenous IGF-1 did not stimulate further growth of a chick embryo.

The method of the present invention provides administration of peptides, for example Fibroblast Growth Factor-2 or Insulin-like Growth Factor-1 at embryonal day 0 (ED0) through embryonal day 4 (ED4) or at embryonal day 18 (ED18) to stimulate muscle stem cells, (satellite cells) to proliferate and increase their cell number. It is exemplified herein that the methods of the present invention provide a surprising and unexpected improvement in poultry performance, particularly in the increase in muscle mass through hyperplasia.

Compositions

One embodiment of the present invention encompasses the use of various types of compounds to improve performance and increase muscle weight in poultry. In a particular embodiment, the present invention can encompass methods utilizing proteins. These proteins are used according to the methods of the present invention. Examples of such include, but should not be limited to, insulin-like growth factor (IGF), for example but not limited to types 1 and 2, fibroblast growth factor (FGF) for example but not limited to type 1 and 2, hepatocyte growth factor (HGF), platelet-derived growth factor (PDGF), growth hormone (GH), growth hormone releasing factor (GRF), and thyrotropin-releasing factor (TRF), and the like. They can also be synthetically or recombinantly produced. For example, SEQ ID NO. 1 discloses the amino acid sequence of the mature form of human FGF-2, which can be used in the methods of the present invention. SEQ ID NO. 2 discloses the amino acid sequence of the mature form of human IGF-1, which can be used in the methods of the present invention. SEQ ID NO. 3 discloses the amino acid sequence of the mature form of chicken FGF-2, which can be used in the methods of the present invention. SEQ ID NO. 4 discloses the amino acid sequence of the mature form of chicken IGF-1, which can be used in the methods of the present invention. The invention also provides variants of any one of SEQ IDs 1-4.

Compositions for use in the methods of the present invention can include one or more veterinarily, or pharmaceutically acceptable carriers or carriers, all used interchangeably. Such carriers include, without limitation, water, saline, buffered saline, phosphate buffer, alcohol/aqueous solutions, emulsions or suspensions. Also included are ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, histidine-Hel, carbonic acid, tartaric acid, succinic acid, acetic acid, phthalic acid, Tris, trimethylamine hydrochloride, or phosphate buffers. Parenteral carriers can include sodium chloride solution, Ringer's dextrose, dextrose, trehalose, sucrose, lactated Ringer's, or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (e.g., EDTA), inert gases and the like may also be provided in the pharmaceutical carriers. The present invention is not limited by the selection of the carrier. The preparation of these pharmaceutically acceptable compositions, from the above-described components, having appropriate pH, isotonicity, stability and other conventional characteristics, is within the skill of the art. See, e.g., texts such as Remington: The Science and Practice of Pharmacy, 20th ed, Lippincott Williams & Wilkins, pub., 2000; and The Handbook of Pharmaceutical Excipients, $4^{th}$ Edition, eds. R. C. Rowe et al., APhA Publications, 2003. This can include any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others known to those skilled in the art. Stabilizers include albumin, among others known to the skilled artisan. Preservatives include merthiolate, chlorocresol among others known to the skilled artisan.

The active compounds described herein may be administered and prepared as pharmaceutical formulations per se or in the form of pharmaceutically acceptable salts thereof. For example, but not limited to, acid addition salts of acetate, adipate, alginate, aspartate, benzoate, benzenesulfonate, bisulfate, butyrate, citrate, camphorate, camphorsulfonate, cyclopentanepropionate, digluconate, dodecylsulfonate, ethanesulfonate, fumarate, glucoheptanoate, glycerophosphate, hemisulfate, heptanoate, hexanoate, hydrochloride, hydrobromide, hydroiodide, 2 hydroxyethanesulfonate, lactate, maleate, methanesulfonate, 2-naphthalenesulfonate, nicotinate, oxalate, pamoate, pectinate, persulfate, 3-phenylproprionate, picrate, pivalate, propionate, succinate, tartrate, thiocyanatetosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids for example but not limited to arginine, lysine etc.

Target of the Invention, Methods of Delivery, Dosages

The term "in ovo", as used herein, refers to an avian contained within an egg prior to hatch. The present invention may be practiced with any type of avian egg, including but not limited to chicken, turkey, duck, goose, quail, and pheasant eggs. Based on the type of avian egg, however, the incubation times in ovo will vary.

As a matter of reference, avian eggs that are laid are considered to be in an inert stage where there is not yet any embryologic development. This stage is called ED0 and can be stored in this stage from 0-21 days, all of which are considered ED0. The eggs at ED0 are placed in an incubator at approximately 99 degrees Fahrenheit by which the heat starts the development of the embryo. The eggs are incubated until embryonal day 18 at which point there is a mature, developed embryo ready to hatch. The eggs are then set in hatching trays for the next three days, up to and including ED21, at which point the eggs hatch into chicks. These chicks then are grown to market age at which point they are processed. Thirty-five days post-hatch for the Cobb breed or forty-two days post-hatch for the Ross breed are considered the grow-out period, anything earlier is considered undesirable for the poultry industry.

The term "in ovo administration", as used herein, refers to means which transports the composition of the invention through the shell of the avian egg, particularly by piercing the egg shell and delivering the treatment to the interior of the egg. The site of injection can be within the region defined by the amnion, including the amniotic fluid and the embryo itself, in the yolk sac, in the albumen or in the air cell. For practicing the present invention, injection into the air cell is preferred. The mechanism of injection is not critical, but it is preferred that the method not unduly damage the tissues and organs of the embryo or the extra-embryonic membranes surrounding it so that the treatment will not unduly decrease hatch rate.

In another embodiment, the methods of the present invention may be carried out on any avian subject, including but not limited to, chickens, turkeys, ducks, geese, quail and pheasant, or any other domesticated fowl.

Eggs treated by the method of the present invention are treated by way of in ovo injection during the first or last quarter of incubation, as defined herein In one embodiment of the present invention the eggs are treated between embryonal day 0 (ED0) and embryonal day 18 (ED18). In one embodiment the eggs are treated during early development, preferably between about ED0 and ED4. In one embodiment, the eggs are treated on or about ED0. In one embodiment, the eggs are treated on or about ED1. In one embodiment, the eggs are treated on or about ED2. In one embodiment, the eggs are treated on or about ED3. In one embodiment, the eggs are treated on or about ED4. In one embodiment, the eggs are treated in the last quarter of incubation. In one embodiment, the eggs are treated on or about ED18 (embryonic day 18). As noted, however, these incubation times listed are those of chicken eggs. Other avian egg incubation times do vary. One of skill in the art will recognize this fact and be able to adjust accordingly.

In general, selection of the appropriate "effective amount" or dosage for the compositions used in the methods of the present invention may be based upon the identity of the composition(s) employed. The presence of additional components in the compositions may also affect the dosages and amounts of the compositions. Such selection, and upward or downward adjustment of the effective dose, is well within the skill of the art. The amount of composition required to induce the desired effect in the subject, without significant adverse side effects, varies depending upon these factors. Suitable doses are readily determined by persons skilled in the art.

Recombinant Techniques

In one embodiment of the methods of the present invention, the composition may comprise a recombinant protein. Such recombinant proteins could be generated from a vector and a heterologous insert encoding for the protein. The heterologous inserts in some embodiments comprise one or more nucleic acid sequences encoding the amino acid sequences of the instant invention, e.g., SEQ ID NOs: 1-4, or variants thereof. The insert may optionally comprise a heterologous promoter, such as, for example, synthetic promoters known in the art. Alternatively, the promoters of the host vector may exert transcriptional control over the expression of the inserts. Suitable non-limiting examples of promoters (which may be native or heterologous, depending on the choice of the vector) are H6 vaccinia promoter, I3L vaccinia promoter, 42K poxyiral promoter, 7.5K vaccinia promoter, and Pi vaccinia promoter.

There are several known methods or techniques that can be used to clone and express the nucleotide sequences of the compositions utilized in the methods of the present invention. For example, the sequences can be isolated as restriction fragments and cloned into cloning and/or expression vectors. The sequences can also be PCR amplified and cloned into cloning and/or expression vectors, or they can be cloned by a combination of these two methods. Standard molecular biology techniques known in the art, and not specifically described, can be generally followed as described in Sambrook et al., *Molecular Cloning: A Laboratory Manual*, Cold Spring Harbor Laboratory Press, New York (1989); Ausubel et al., *Current Protocols in Molecular Biology*, John Wiley and Sons, Baltimore, Md. (1989); Perbal, *A Practical Guide to Molecular Cloning*, John Wiley & Sons, New York (1988); Watson et al., *Recombinant DNA*, Scientific American Books, New York; Birren et al (eds) *Genome Analysis: A Laboratory Manual Series, Vols. 1-4* Cold Spring Harbor Laboratory Press, New York (1998); and methodology set forth in U.S. Pat. Nos. 4,666,828; 4,683,202; 4,801,531; 5,192,659 and 5,272,057. Polymerase chain reaction (PCR) is carried out generally as described in *PCR Protocols: A Guide to Methods and Applications*, Academic Press, San Diego, Calif. (1990).

The methods of the present invention can encompass the use of prokaryotic and eukaryotic expression systems, including vectors and host cells, which may be used to express both truncated and full-length forms of the recombinant polypeptides expressed by the nucleotide sequences of the present invention. A variety of host-expression vector systems may be utilized to express the polypeptides utilized in the methods of the present invention. Such host-expression systems also represent vehicles by which the coding sequences of interest may be cloned and subsequently purified. The present invention further provides for host cells which may, when transformed or transfected with the appropriate vector or nucleotide sequence, express the encoded polypeptide gene product of the invention. Such host cells include, but are not limited to, microorganisms such as bacteria (e.g., *E. coli, Bacillus subtilis, Corynebacterium*) transformed with recombinant bacteriophage DNA, plasmid DNA or cosmid DNA expression vectors containing coding sequences; yeast (e.g., *Saccharomyces, Pichia*) transformed with recombinant yeast expression vectors containing the gene product coding sequences; insect cell systems infected with recombinant virus expression vectors (e.g., baculovirus) containing the coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

The vectors that can be utilized in the methods of the present invention can be derived from, but not limited to, bacterial plasmids, from bacteriophage, from yeast episomes, from yeast chromosomal elements, from mammalian viruses, from mammalian chromosomes, and from combinations thereof, such as those derived from plasmid and bacteriophage genetic elements including, but not limited to, cosmids and phagemids.

Vectors that can be utilized in the methods of the present invention can be used for the expression of polypeptides. Generally, the vectors of the invention include cis-acting regulatory regions operably linked to the polynucleotide that encodes the polypeptides to be expressed. The regulatory regions may be constitutive or inducible. Appropriate trans-acting factors are supplied by the host by an in vitro translation system, by a complementing vector, or by the vector itself upon introduction into the host.

The vectors that can be utilized in the methods of the invention can include any elements typically included in an expression or display vector, including, but not limited to, origin of replication sequences, one or more promoters, antibiotic resistance genes, leader or signal peptide sequences, various tag sequences, stuffer sequences that may encode a gene whose polypeptide confers antibiotic resistance, restriction sites, ribosome binding sites, translational enhancers (sequences capable of forming stem loop structures for mRNA stability post-transcription), sequences that encode amino acids lacking a stop codon, and sequences that encode a bacterial coat protein.

To facilitate isolation of a peptide for use in the methods of the present invention, a fusion polypeptide can be made, wherein the peptide or a specific fragment thereof is linked to a heterologous polypeptide, which enables isolation by affinity chromatography. Preferably, a fusion polypeptide is made using one of the expression systems known to those of skill in the art. For example, the polynucleotide encoding for the peptide or a specific fragment thereof is linked at either its 5' or 3' end to a nucleic acid encoding a heterologous polypeptide. The nucleic acids are linked in the proper codon reading frame to enable production of a fusion polypeptide, wherein the amino and/or carboxyl terminus of the peptide or portion thereof is fused to a heterologous polypeptide which allows for the simplified recovery of the antigen as a fusion polypeptide. The fusion polypeptide can also prevent the antigen from being degraded during purification. In some instances, it can be desirable to remove the heterologous polypeptide after purification. Therefore, it is also contemplated that the fusion polypeptide comprise a cleavage site at the junction between the peptide and the heterologous polypeptide. The cleavage site consists of an amino acid sequence that is cleaved with an enzyme specific for the amino acid sequence at the site. Examples of such cleavage sites that are contemplated include the enterokinase cleavage site which is cleaved by enterokinase, the factor Xa cleavage site which is cleaved by factor Xa, and the GENENASE cleavage site which is cleaved by GENENASE (GENENASE is a trademark of New England Biolabs; Beverly, Mass.).

An example of a prokaryote expression system for producing the peptide or a specific fragment thereof is the Glutathione S-transferase (GST) Gene Fusion System (Amersham Pharmacia Biotech; Piscataway, N.J.). Another method for producing the fusion protein is a method which links in-frame with the cDNA encoding the antigen, a DNA sequence encoding a polyhistidine tag. Said tag allows for purification of the fusion polypeptide by metal affinity chromatography, preferably nickel affinity chromatography. The Xpress System (Invitrogen; Carlsbad, Calif.) is an example of a commercial kit available for making and then isolating polyhistidine-polypeptide fusion proteins.

Also, the pMAL Fusion and Purification System (New England Biolabs; Beverly, Mass.) is another example of a means for making a fusion polypeptide, wherein a maltose-binding protein (MBP) is fused to the peptide or a specific fragment thereof. The MBP facilitates isolation of the fusion polypeptide by amylose affinity chromatography.

Other fusion partners, and methods for generating such fusions, are readily available, and known to those of skill in the art. Said fusions can be used in their entirety as the composition used in the methods of the present invention, or they can be cleaved at the junction between the peptide and the heterologous polypeptide.

Alternatively, the fusion protein can serve to extend the half-life of the peptide used in the methods of the present invention, or a specific fragment thereof. Examples of suitable fusion proteins include antibodies or fragments thereof, including the Fc portion of an antibody. Albumin can also serve as a fusion partner to extend the half life of compositions utilized in the methods of the present invention, as can transferrin. Other proteins can be utilized as fusion partners to extend the half-life of compositions utilized in methods of the present invention, and are known to those of ordinary skill in the art.

Methods of fusing polypeptides utilized in the methods of the present invention with fusion partners can include chemical coupling, also known as crosslinking, or bioconjugation. Targets for crosslinking methods include the protein functional groups of primary amines, carboxyls, sulfhydryls, and carbonyls. Examples of suitable crosslinkers include disuccinimidyl suberate (DDS) and sulfosuccinimidyl 4-(N-maleimidomethyl)cyclohexane-1-carboxylate (Sulfo-SMCC). Polypeptides utilized in the methods of the present invention can also be joined to fusion partners by means of genetic coupling. This can occur when two separate genes originally encoding for two separate proteins are joined. Translation of this fusion gene results in a single polypeptide, known as a fusion or chimeric protein. Methods of creating fusion proteins by chemical or genetic coupling are readily know to those of skill in the art, and should not be limited to those specifically disclosed herein.

Overall, this invention provides a method demonstrating the ED0-ED4 and about the last quarter of embryonal incubation time point of intervention with substrates results in surprising and unpredictable performance gains in market age birds. These surprising results can be utilized for commercial value to the poultry industry. Additionally, the method further provides that an increase in the leg muscles in synchronous with the increase in breast muscle resulting in a sturdier and a healthier bird free of ambulatory and associated problems. Overall the muscle weight gains exemplified herein shows increases that have not been seen in the poultry industry thus far.

The present invention is further illustrated and supported by the following examples. However, these examples should in no way be considered to further limit the scope of the invention. To the contrary, one having ordinary skill in the art would readily understand that there are other embodiments, modifications, and equivalents of the present invention without departing from the spirit of the present invention and/or the scope of the claims.

EXAMPLES

Example 1

Effect of FGF-2 or IGF-1 Given in Ovo on Day 35 Broiler Performance

The objective of this study was to evaluate Day 35 breast weight and body weight after Fibroblast Growth Factor-2 (FGF-2) or Insulin-like Growth Factor-1 (IGF-1) administration in ovo into the air cell on Embryonic Day 4 (ED4).

In Ovo Phase:

This study included four treatment groups: T01 (PBS control; up to 40 birds were placed), T02 (high dose IGF; up to 40 birds were placed), T03 (high dose FGF-2; up to 40 birds were placed) and T04 (very high dose FGF-2; up to 30 birds were placed.). Please see Table 1.

TABLE 1

| Study Design | |
|---|---|
| Treatment Group | Compound |
| T01 | Control (PBS) |
| T02 | IGF (200 ng) |
| T03 | FGF-2 (40 ng) |
| T04 | FGF-2 (120 ng) |

Treatments were administered in ovo on ED4 using the following procedure:
1. The air cell of each egg was located by candling and marked in pencil.
2. A hole was punched in the center of the area marked by the circle using an 18 G needle.
3. The assigned treatment was administered in a 100 µL volume by dropping into the punched hole using an 18 G ¼" needle inserted to the hub or a Gilman pipette with a plastic pipette tip.
4. The punched hole was sealed with hot glue from a glue gun.
5. Eggs were returned to the incubator.

All eggs were set in a commercial incubator. The assigned treatment was administered in the air cell of each egg on Embryonic Day (ED4). Following treatment administration, the eggs were returned to the assigned flat and level in the incubator in a randomized fashion. On ED18, eggs were candled and viable eggs were transferred to the assigned hatcher basket.

On ED18, 30 eggs each from the each treatment group were collected. Pectoralis major breast muscles were extracted. Breast muscle weights were recorded for each egg.

Grow-Out Phase:

At hatch (Day 0), all remaining viable chicks were individually weighed, necktagged and all birds were commingled in a single floor pen. Birds had ad libitum access to feed and water throughout the study.

Observations were performed twice daily for general flock condition, lighting, water, feed, ventilation and unanticipated events. All deads and culls were weighed and necropsied to determine bird sex and cause of death.

Individual bird weights were recorded on Days 7, 14, 28 and 35. Following collection of individual body weights on Day 35, all surviving birds were euthanized and the boneless skinless left breast half was removed and weighed. All breast weights were recorded. Sex was also determined and recorded for each bird.

Analysis

The primary variables for analysis were breast weight and average daily gain. Secondary variables for analysis included carcass weight, ratio of carcass weight to live weight and ratio of breast weight to carcass weight. Body weight data were statistically analyzed using a mixed linear model for repeated measures. The model included the fixed effects for treatment, day of study and the treatment by day of study interaction. The random effects included animal within treatment and residual error. Treatment least squares means (LSMean) for body weight and average daily gain for study periods (0-14, 28-34, and 0-34) was estimated from the repeated measures model for body weight. Standard errors of least squares means were estimated and 90% confidence intervals were constructed. Day 35 body weights and carcass data (breast weight, carcass weight, ratio of breast weight to carcass weight, ratio of carcass weight to live weight) were analyzed using a mixed linear model. The models contained fixed effects for sex, treatment, and sex by treatment interaction, and the random effect for residual error. Least squares means were used as estimates of treatment means. Standard errors of least squares means were estimated and 90% confidence intervals were constructed.

Results:

Least square mean body weights on Day 35 were 2097.8 g, 2136.3 g, 2222.7 g and 2092.5 g for T01-T04, respectively. The analysis of Day 35 *P. major* breast muscle weight is presented in Table 2.

TABLE 2

Analysis of Day 35 Breast Weight (g)

| Treatment | Number of Animals | LSMean | Std. Error | Range | % Δ from T01 Control | P-value vs T01 Control |
|---|---|---|---|---|---|---|
| T01 Control (PBS) | 28 | 156.2 | 4.56 | 107 to 201.4 | | |
| T02 IGF-1 (200 ng) | 31 | 167.1 | 4.33 | 111.2 to 213.1 | 7.0 | 0.0856 |
| T03 FGF-2 (40 ng) | 29 | 167.4 | 4.48 | 106.1 to 199.9 | 7.2 | 0.0836 |
| T04 FGF-2 (120 ng) | 19 | 154.4 | 9.87 | 40.8 to 217.4 | −1.1 | Not significant |

This study evaluated the administration of IGF and FGF-2 in ovo. Treatments were administered in ovo in the air cell on ED4. Administration of IGF (200 ng) by this route at this stage of embryonic development resulted in a 7.0% increase in breast muscle weight on Day 35. Administration of a low dose of FGF-2 (40 ng) under the same conditions resulted in a 7.2% increase in breast muscle mass on Day 35. However, administration of a 3× dose of FGF-2 (120 ng) resulted in a 1.1% decrease in Day 35 breast muscle weight. Thus, administration of 200 ng of IGF or 40 ng of FGF-2 in ovo into the air cell of eggs on ED4 resulted in ≥7.0% increase in total breast muscle weight on Day 35 compared to saline controls.

Example 2

Effect of FGF-2 or IGF Given in Ovo on Muscle Development and ED18 Embryo Breast Muscle Weight The objective of this study was to evaluate the effect of human FGF-2 or IGF-1 given in ovo on ED4 on muscle development and ED18 embryo breast muscle weight.

This study included five treatment groups: T01 (PBS control), T02 (200 ng IGF), T03 (100 ng IGF), T04 (50 ng IGF) and T05 (40 ng FGF). See Table 3 below.

TABLE 3

Study Design

| Treatment Group | Compound | Total ED18 Eggs Used |
|---|---|---|
| T01 | Control (PBS) | Up to 30 |
| T02 | IGF (200 ng) | Up to 30 |
| T03 | IGF (100 ng) | Up to 30 |
| T04 | IGF (50 ng) | Up to 30 |
| T05 | FGF (40 ng) | Up to 30 |

Treatments (Table 3) were administered in ovo on ED4 using the following procedure:

1. The air cell of each egg was located by candling and marked in pencil.
2. A hole was punched in the center of the area marked by the circle using an 18 G needle.
3. The assigned treatment was administered in a 100 μL volume by dropping into the punched hole using an 18 G ¼" needle inserted to the hub or a Gilman pipette with a plastic pipette tip.
4. The punched hole was sealed with hot glue from a glue gun.
5. Eggs were returned to the incubator.

All eggs were set in a commercial incubator. The assigned treatment was administered in the air cell of each egg on ED4. Following treatment administration, the eggs were returned to the assigned flat and level in the incubator in a randomized fashion. On ED18, up to 30 eggs of each treatment group were removed. Body weights were recorded and *P. major* breast muscles were harvested. Breast muscle weights were recorded for each egg.

Analysis

The primary variable for analysis was breast weight. Breast weight data was statistically analyzed using a mixed linear model. The model contained fixed effects for treatment, and the random effect for residual error. Least squares means were used as estimates of treatment means. Standard errors of least squares means were estimated and 90% confidence intervals were constructed. A priori contrasts were used to assess treatment differences using Fisher's protected LSD provided that the treatment effect is significant. Treatment differences were assessed at the 10% level of significance (P<0.10).

Results

The analysis of the breast muscle weight on ED18 is presented in Table 4. A priori contrasts are presented in Table 5.

TABLE 4

Analysis of Breast Muscle Weight on ED18

| Treatment | # Animals | LS mean (g) | Std. Error | 90% confidence limits | Range | % Δ from T01 |
|---|---|---|---|---|---|---|
| T01 (Control 0 ng) | 29 | 0.19 | 0.006 | (0.18, 0.2) | 0.1 to 0.26 | |
| T02 (IGF 200 ng) | 26 | 0.24 | 0.006 | (0.23, 0.25) | 0.19 to 0.3 | 28.60 |
| T03 (IGF 100 ng) | 26 | 0.25 | 0.007 | (0.24, 0.26) | 0.18 to 0.32 | 33.07 |
| T04 (IGF 50 ng) | 29 | 0.25 | 0.006 | (0.24, 0.26) | 0.19 to 0.32 | 30.60 |
| T05 (FGF 40 ng) | 26 | 0.24 | 0.006 | (0.22, 0.25) | 0.18 to 0.32 | 24.13 |

TABLE 5

A priori Contrasts for Breast Muscle Weight on ED18

| Contrast | Least Squares Means Difference | Standard Error | P value | Significant at 0.10 level |
|---|---|---|---|---|
| T01 (Control 0 ng) Vs T02 (IGF 200 ng) | −0.05 | 0.009 | 0.0000 | YES |
| T01 (Control 0 ng) Vs T03 (IGF 100 ng) | −0.06 | 0.009 | 0.0000 | YES |
| T01 (Control 0 ng) Vs T04 (IGF 50 ng) | −0.06 | 0.009 | 0.0000 | YES |
| T01 (Control 0 ng) Vs T05 (FGF 40 ng) | −0.05 | 0.009 | 0.0000 | YES |
| T02 (IGF 200 ng) Vs T03 (IGF 100 ng) | −0.01 | 0.009 | 0.3630 | NO |
| T02 (IGF 200 ng) Vs T04 (IGF 50 ng) | −0.00 | 0.009 | 0.6625 | NO |
| T02 (IGF 200 ng) Vs T05 (FGF 40 ng) | 0.01 | 0.009 | 0.3297 | NO |
| T03 (IGF 100 ng) Vs T04 (IGF 50 ng) | 0.00 | 0.009 | 0.6130 | NO |
| T03 (IGF 100 ng) Vs T05 (FGF 40 ng) | 0.02 | 0.009 | 0.0715 | YES |
| T04 (IGF 50 ng) Vs T05 (FGF 40 ng) | 0.01 | 0.009 | 0.1595 | NO |

LSMean breast muscle weights on ED18 were 0.19, 0.24, 0.25, 0.25 and 0.24 g for T01-T05, respectively. All IGF (T02-T04) and FGF (T05) dose groups had significantly higher ED18 breast muscle weights compared to saline controls (T01). In addition, IGF at 100 ng (T03) had significantly higher ED18 breast muscle weight compared to FGF at 40 ng (T05). There were no significant differences in ED18 breast muscle weight among IGF groups.

In ovo administration of IGF at 50-200 ng/egg in the air cell on ED4 resulted in 28-33% increases in breast muscle mass on ED18. In ovo administration of FGF at 40 ng/egg in the air cell on ED4 resulted in a 24% increase in breast muscle mass on ED18.

Example 3

Effect of FGF-2 Given at ED4 in Ovo on Muscle Development and ED18 Embryo Breast Muscle Weight The objective of this study was to evaluate the effect of human FGF-2 administered in ovo on ED4 on gene upregulation and muscle hyperplasia.

This study included four treatment groups: T01 (PBS with pen-strep control), T02 (FGF-2, 10 ng), T03 (FGF-2, 20 ng) and T04 (FGF-2, 40 ng).

TABLE 6

Study Design

| Treatment Group | Compound | Total ED18 Eggs Used |
|---|---|---|
| T01 | Control (PBS) | Up to 30 |
| T02 | FGF-2 (10 ng) ("Low") | Up to 30 |
| T03 | FGF-2 (20 ng) ("Medium") | Up to 30 |
| T04 | FGF-2 (40 ng) ("High") | Up to 30 |

Treatments were administered in ovo on ED4 using the following procedure:
1. The air cell of each egg was located by candling and marked in pencil.
2. A hole was punched in the center of the area marked by the circle using an 18 G needle.
3. The assigned treatment was administered in a 100 μL volume by dropping into the punched hole using an 18 G ¼" needle inserted to the hub or a Gilman pipette with a plastic pipette tip.
4. The punched hole was sealed with hot glue from a glue gun.
5. Eggs were returned to the incubator.

Eggs were set in a commercial incubator. The assigned treatment was administered in the air cell of each egg on ED4. Following treatment administration, the eggs were returned to the assigned flat and level in the incubator. On ED18, up to 30 eggs of each treatment group were removed. Body weights were recorded and *P. major* breast muscles were harvested. Breast muscle weights were recorded for each egg and breast tissues were harvested for histopathology and genomic analysis.

Eggs on two flats within the incubator were assigned to treatment according to a completely randomized design with one-way treatment structure.

Pertinent Variables Measured Body Weight and ED18 Breast Muscle

On ED18, up to 30 eggs each from the each treatment group were collected. Individual embryo body weights were recorded then *P. major* breast muscles were extracted. The weight of each embryo's *P. major* left breast muscle was weighed and recorded.

Gene Analysis

RNA was extracted from breast muscle tissues. RNA samples were analyzed by qPCR for glypican-1 and myogenin gene expression. The primers are listed in Table 7.

TABLE 7

Primers Used

| Primers | Sequences | Gene Name | GenBank No. | Product size (bp) |
|---|---|---|---|---|
| turkey MyoD-F | GATGGCATGATGGAGTACAG (SEQ ID NO. 5) | myogenic factor 1 | AY641567 | 201 |
| turkey MyoD-R | AGCTTCAGCTGGAGGCAGTA (SEQ ID NO. 6) | (turkey) | | |
| turkey Myogenin-F | CCTTTCCCACTCCTCTCCAAA (SEQ ID NO. 7) | *Meleagris gallopavo* myogenin | AY560111 | 177 |
| turkey Myogenin-R | GACCTTGGTCGAAGAGCAACT (SEQ ID NO. 8) | (turkey) | | |
| Glypican1-F | ACATCGGGAATGATGTGGAT (SEQ ID NO. 9) | glypican-1 (chicken) | L29089 | 208 |
| Glypican1-R | AAGAGGAGGAAGGCAGAAGG (SEQ ID NO.10) | | | |
| Syndecan4-F | CCAACAGCAGCATCTTTGAA (SEQ ID NO.11) | syndecan-4 (chicken) | NM001007869 | 155 |
| Syndecan4-R | GATGGGTTTCTTCCCAAGGT (SEQ ID NO. 12) | | | |

Amplification and detection were carried out with the Mx3000P system (Stratagene) and RT² SYBR® Green qPCR Mastermix (SABioscience). The levels of individual transcripts were normalized to those of GAPDH.

Results: Gene Expression

Figure 5:
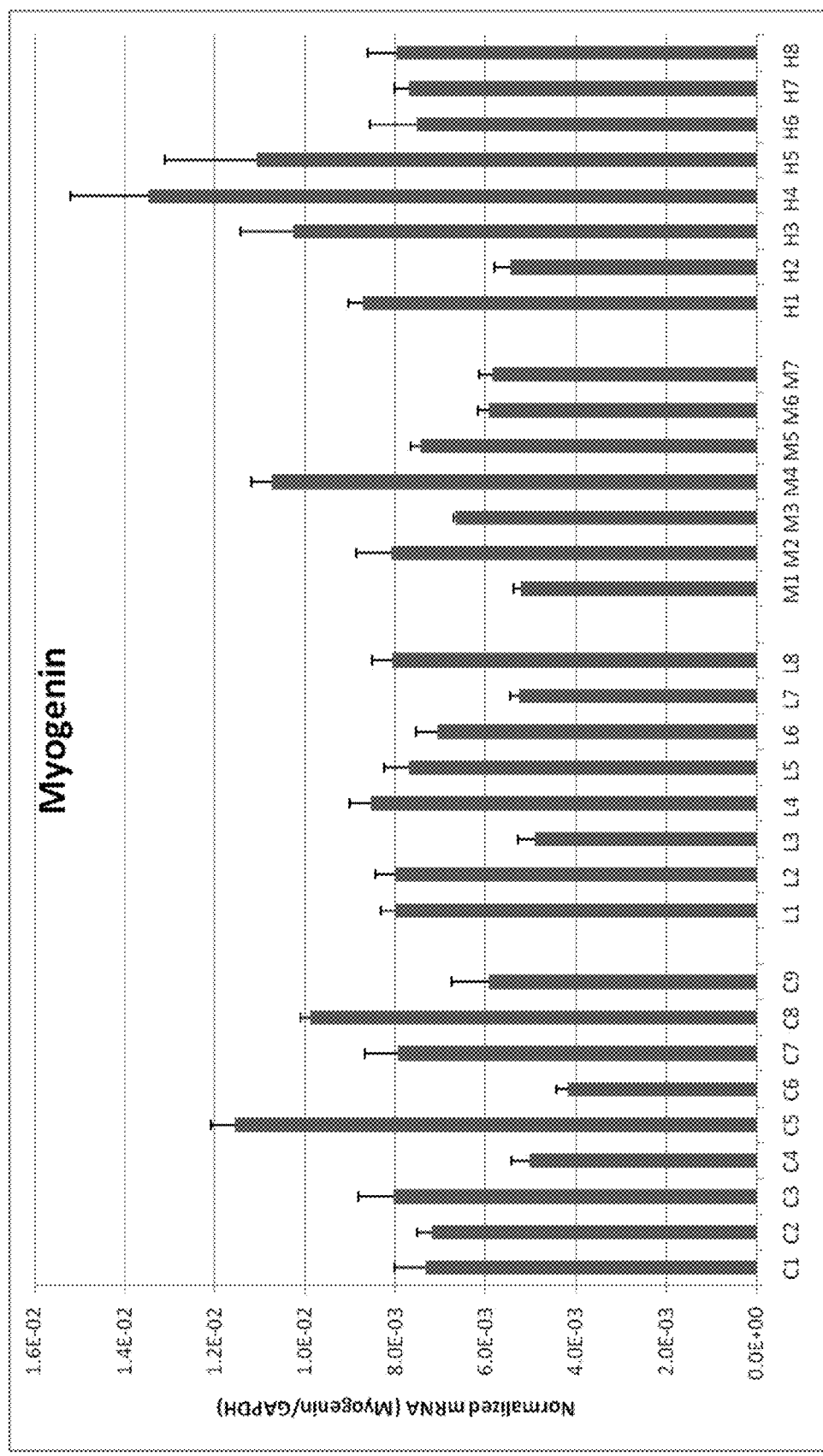
FIG. 5: Graphical representation of gene expression data of ED18 breast muscle after in ovo treatment at ED4 with different concentrations (10 ng, 20 ng and 40 ng) of FGF-2. Expression of Myogenin transcripts were measured and compared to GAPDH expression levels after RNA extraction and qPCR analysis.
Figure 6:
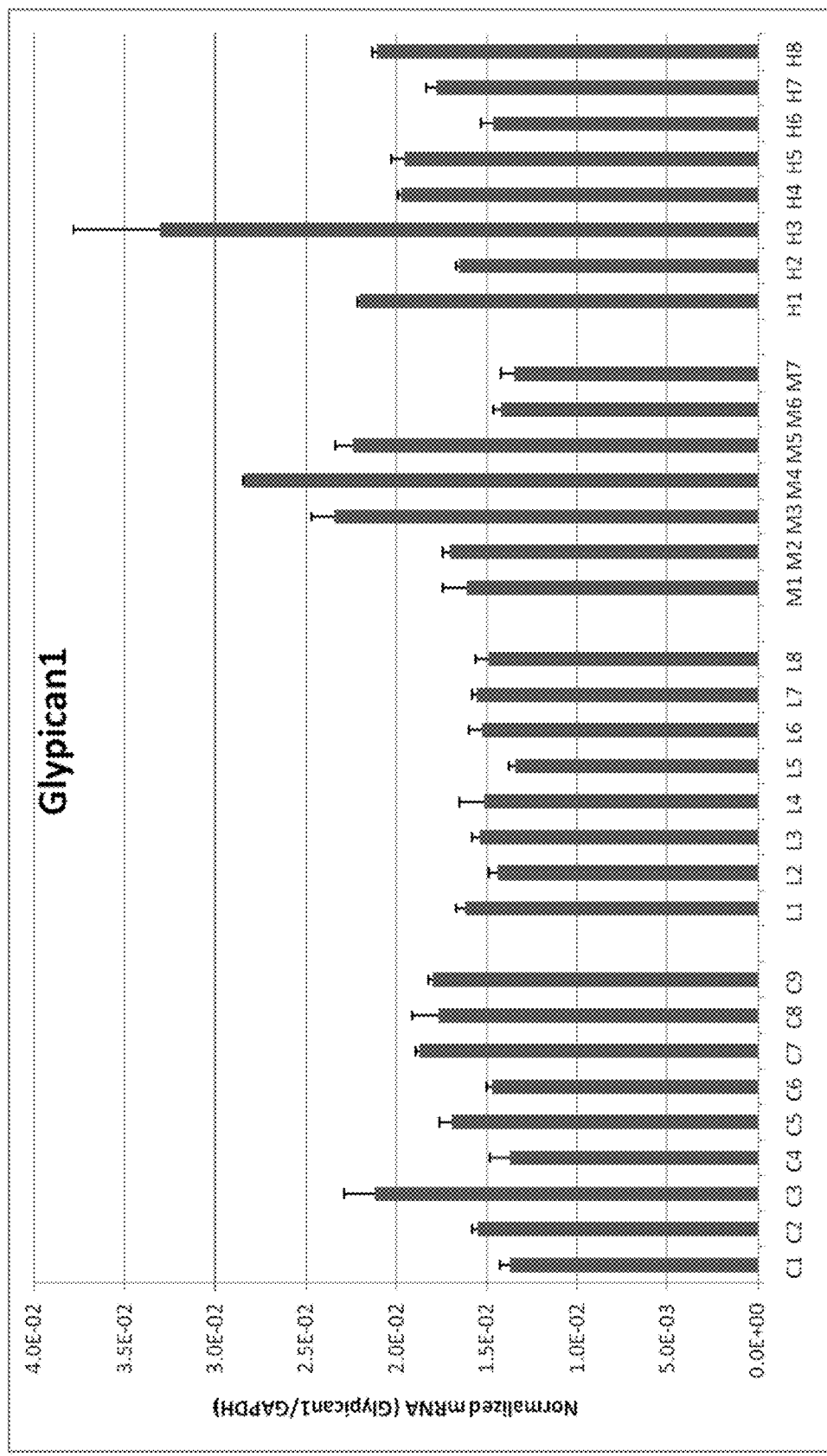
FIG. 6: Graphical representation of gene expression data of ED18 breast muscle after in ovo treatment at ED4 with different concentrations (10 ng, 20 ng and 40 ng) of FGF-2. Expression of Glypican-1 transcripts were measured and compared to GAPDH expression levels after RNA extraction and qPCR analysis.
Figure 7:
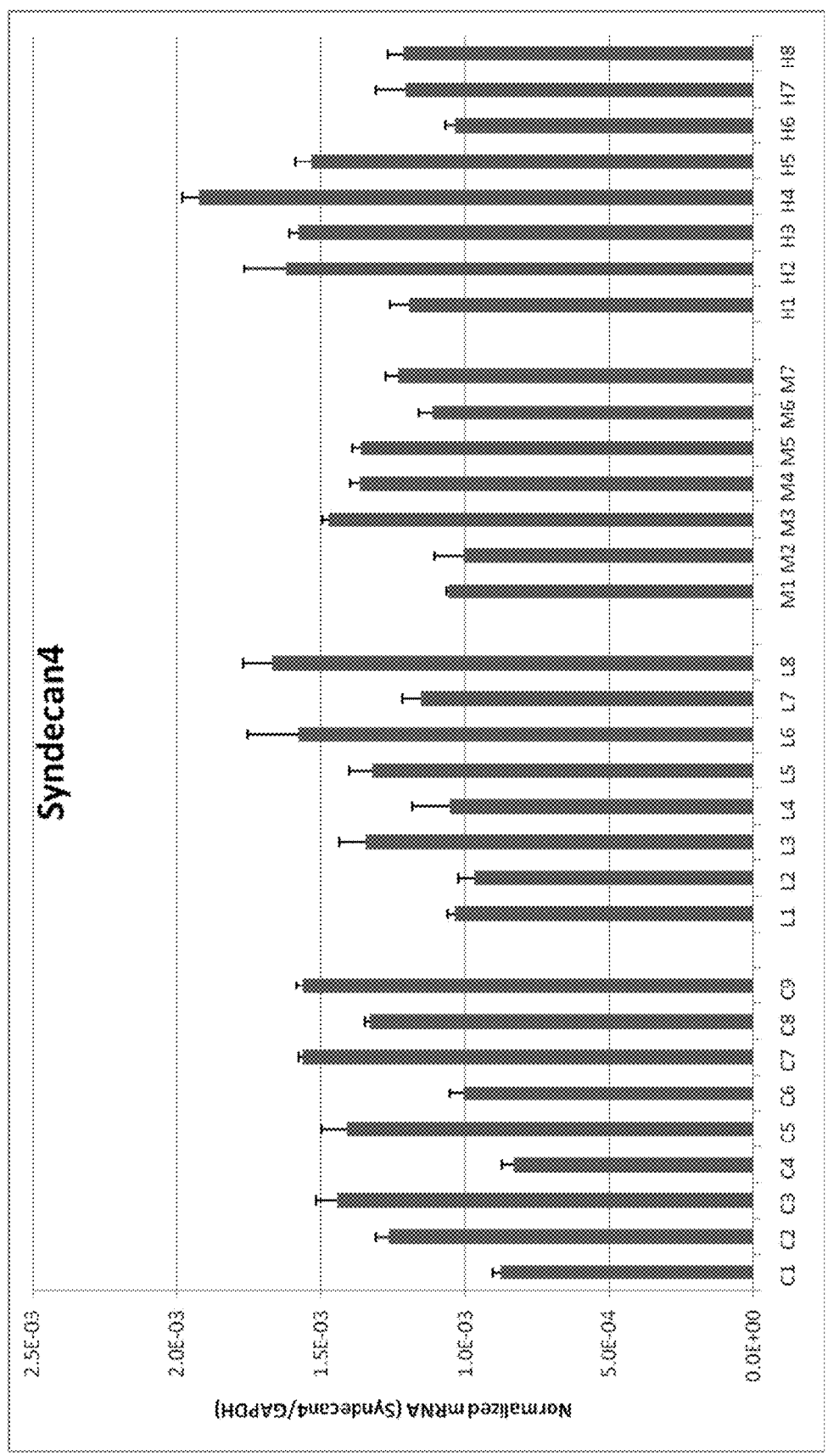
FIG. 7: Graphical representation of gene expression data of ED18 breast muscle after in ovo treatment at ED4 with different concentrations (10 ng, 20 ng and 40 ng) of FGF-2. Expression of Syndecan-4 transcripts were measured and compared to GAPDH expression levels after RNA extraction and qPCR analysis.
Figure 8:
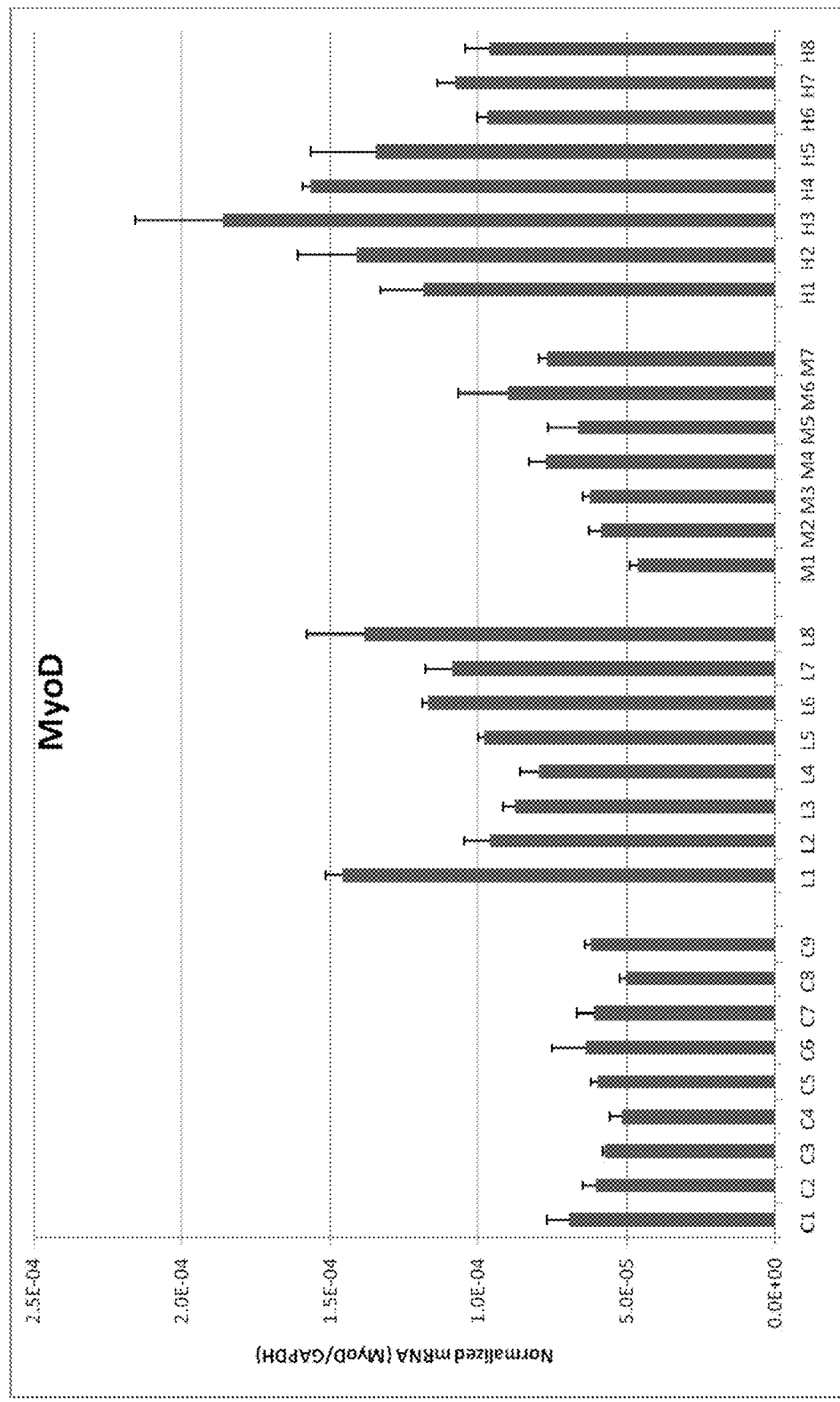
FIG. 8: Graphical representation of gene expression data of ED18 breast muscle after in ovo treatment at ED4 with different concentrations (10 ng, 20 ng and 40 ng) of FGF-2. Expression of MyoD transcripts were measured and compared to GAPDH expression levels after RNA extraction and qPCR analysis.

MyoD, Syndecan4, Myogenin and Glypican-1 gene expression data are presented in FIGS. 5-8. These data show the gene expression levels of transcripts measured by quantitative real time PCR. Each bar represents the pooled samples with equal amount RNAs of 3 or 4 embryos from the treatment groups of "C", "L", "M", and "H". The primers used for the qRT-PCR are listed in Table 7. The quantification and pooling information for the RNAs is shown in Table 8.

TABLE 8

RNA Quantification and Pooling Data

| Pooled ID | Sample ID | Conc. (ng/µl) | Total RNA (ng) | RNA | Total vol. (µl) | dH$_2$O (µl) |
|---|---|---|---|---|---|---|
| C1 | C1 | 1478.01 | 2250 | 1.5 | 5.1 | 2.9 |
| | C2 | 1072.7 | 2250 | 2.1 | | |
| | C3 | 1552.97 | 2250 | 1.4 | | |
| C2 | C4 | 1698.19 | 2250 | 1.3 | 4.1 | 3.9 |
| | C5 | 1547.15 | 2250 | 1.5 | | |
| | C6 | 1651.49 | 2250 | 1.4 | | |
| C3 | C7 | 1846.91 | 2250 | 1.2 | 4.9 | 3.1 |
| | C8 | 1532.39 | 2250 | 1.5 | | |
| | C9 | 1029.7 | 2250 | 2.2 | | |
| C4 | C10 | 1012.46 | 2250 | 2.2 | 4.5 | 3.5 |
| | C11 | 2011.77 | 2250 | 1.1 | | |
| | C12 | 2014.74 | 2250 | 1.1 | | |
| C5 | C13 | 846.68 | 2250 | 2.7 | 6.3 | 1.7 |
| | C14 | 1450.33 | 2250 | 1.6 | | |
| | C15 | 1101.63 | 2250 | 2.0 | | |
| C6 | C16 | 1701.42 | 2250 | 1.3 | 5.3 | 2.7 |
| | C17 | 1198.79 | 2250 | 1.9 | | |
| | C18 | 1056.65 | 2250 | 2.1 | | |
| C7 | C19 | 2321.81 | 2250 | 1.0 | 4.6 | 3.4 |
| | C20 | 1138.33 | 2250 | 2.0 | | |
| | C21 | 1396.85 | 2250 | 1.6 | | |
| C8 | C22 | 1844.84 | 2250 | 1.2 | 3.0 | 5.0 |
| | C23 | 2552.5 | 2250 | 0.9 | | |
| | C24 | 2531.31 | 2250 | 0.9 | | |
| C9 | C25 | 1853.24 | 2250 | 1.2 | 4.9 | 3.1 |
| | C26 | 1294.85 | 2250 | 1.7 | | |
| | C27 | 1138.55 | 2250 | 2.0 | | |
| L1 | L1 | 1714.76 | 2250 | 1.3 | 5.3 | 2.7 |
| | L2 | 1737.16 | 2250 | 1.3 | | |
| | L3 | 837.29 | 2250 | 2.7 | | |
| L2 | L4 | 2356.04 | 2250 | 1.0 | 4.3 | 3.7 |
| | L5 | 1532.76 | 2250 | 1.5 | | |
| | L6 | 1231.16 | 2250 | 1.8 | | |
| L3 | L7 | 1261.94 | 2250 | 1.8 | 4.6 | 3.4 |
| | L8 | 1821.18 | 2250 | 1.2 | | |
| | L9 | 1439.08 | 2250 | 1.6 | | |
| L4 | L10 | 1468.23 | 2250 | 1.5 | 4.8 | 3.2 |
| | L11 | 1583.38 | 2250 | 1.4 | | |
| | L12 | 1202.9 | 2250 | 1.9 | | |
| L5 | L13 | 992.9 | 2250 | 2.3 | 5.4 | 2.6 |
| | L14 | 1386.68 | 2250 | 1.6 | | |
| | L15 | 1507.42 | 2250 | 1.5 | | |
| L6 | L16 | 737.22 | 2250 | 3.1 | 6.8 | 1.2 |
| | L17 | 1374.05 | 2250 | 1.6 | | |
| | L18 | 1085.91 | 2250 | 2.1 | | |
| L7 | L19 | 771.92 | 2250 | 2.9 | 6.3 | 1.7 |
| | L20 | 1312.83 | 2250 | 1.7 | | |
| | L21 | 1353.04 | 2250 | 1.7 | | |

TABLE 8-continued

RNA Quantification and Pooling Data

| Pooled ID | Sample ID | Conc. (ng/μl) | Total RNA (ng) | RNA | Total vol. (μl) | dH$_2$O (μl) |
|---|---|---|---|---|---|---|
| L8 | L22 | 1051.72 | 2250 | 2.1 | 8.0 | 0.0 |
|  | L23 | 1326.44 | 2250 | 1.7 |  |  |
|  | L24 | 1298.48 | 2250 | 1.7 |  |  |
|  | L25 | 940.41 | 2250 | 2.4 |  |  |
| M1 | M1 | 1047.83 | 2250 | 2.1 | 7.4 | 0.6 |
|  | M2 | 808.14 | 2250 | 2.8 |  |  |
|  | M3 | 910.33 | 2250 | 2.5 |  |  |
| M2 | M4 | 1167.33 | 2250 | 1.9 | 5.3 | 2.7 |
|  | M5 | 1324.81 | 2250 | 1.7 |  |  |
|  | M6 | 1363.86 | 2250 | 1.6 |  |  |
| M3 | M7 | 1580.88 | 2250 | 1.4 | 5.6 | 2.4 |
|  | M8 | 1321.94 | 2250 | 1.7 |  |  |
|  | M9 | 901.17 | 2250 | 2.5 |  |  |
| M4 | M10 | 1978.38 | 2250 | 1.1 | 5.2 | 2.8 |
|  | M11 | 923.52 | 2250 | 2.4 |  |  |
|  | M12 | 1369.07 | 2250 | 1.6 |  |  |
| M5 | M13 | 1453.51 | 2250 | 1.5 | 6.1 | 1.9 |
|  | M14 | 1534.18 | 2250 | 1.5 |  |  |
|  | M15 | 719.38 | 2250 | 3.1 |  |  |
| M6 | M16 | 1377.96 | 2250 | 1.6 | 7.1 | 0.9 |
|  | M17 | 1192.65 | 2250 | 1.9 |  |  |
|  | M18 | 1216.15 | 2250 | 1.9 |  |  |
|  | M19 | 1325.06 | 2250 | 1.7 |  |  |
| M7 | M20 | 1941.19 | 2250 | 1.2 | 6.7 | 1.3 |
|  | M21 | 1352.06 | 2250 | 1.7 |  |  |
|  | M22 | 1123.78 | 2250 | 2.0 |  |  |
|  | M23 | 1200.65 | 2250 | 1.9 |  |  |
| H1 | H1 | 1377.98 | 2250 | 1.6 | 6.4 | 1.6 |
|  | H2 | 1010.01 | 2250 | 2.2 |  |  |
|  | H3 | 874.64 | 2250 | 2.6 |  |  |
| H2 | H4 | 1477.56 | 2250 | 1.5 | 6.3 | 1.7 |
|  | H5 | 856.37 | 2250 | 2.6 |  |  |
|  | H6 | 1038.46 | 2250 | 2.2 |  |  |
| H3 | H7 | 1569.6 | 2250 | 1.4 | 4.5 | 3.5 |
|  | H8 | 1261.54 | 2250 | 1.8 |  |  |
|  | H9 | 1692.4 | 2250 | 1.3 |  |  |
| H4 | H10 | 1642.35 | 2250 | 1.4 | 5.4 | 2.6 |
|  | H11 | 1482.61 | 2250 | 1.5 |  |  |
|  | H12 | 881.48 | 2250 | 2.6 |  |  |
| H5 | H13 | 1558.46 | 2250 | 1.4 | 5.6 | 2.4 |
|  | H14 | 948.23 | 2250 | 2.4 |  |  |
|  | H15 | 1274.09 | 2250 | 1.8 |  |  |
| H6 | H16 | 2057.24 | 2250 | 1.1 | 5.8 | 2.2 |
|  | H17 | 1325.14 | 2250 | 1.7 |  |  |
|  | H18 | 759.99 | 2250 | 3.0 |  |  |
| H7 | H19 | 1053.75 | 2250 | 2.1 | 5.8 | 2.2 |
|  | H20 | 1556.22 | 2250 | 1.4 |  |  |
|  | H21 | 1008.87 | 2250 | 2.2 |  |  |
| H8 | H22 | 1028.54 | 2250 | 2.2 | 6.2 | 1.8 |
|  | H23 | 991.46 | 2250 | 2.3 |  |  |
|  | H24 | 1261.66 | 2250 | 1.8 |  |  |

Results

In ovo administration of FGF-2 at 10-40 ng in the air cell on ED4 resulted in up to 26% increase in breast muscle weight on ED18 compared to controls. Breast muscle as a percentage of body weight also increased significantly. Body weight at ED18 was not affected by FGF-2 administration in ovo on ED4. The morphologic increase in breast weight was corroborated by biomarkers such as Glypican-1 and Myogenin which were upregulated nearly 1.5 to 2 times.

Average body weights for ED18 embryos were 28.99 g, 29.13 g, 28.98 g and 28.68 g for T01-T04 respectively. Average left breast muscle weights on ED18 were 0.195 g, 0.233 g, 0.247 g and 0.248 g for T01-T04 respectively. All FGF-2 treatment groups (T02-T04) had significantly heavier breast muscles compared to T01 controls. The percentage of body weight represented by the *P. major* breast muscles (left muscle×2) were 1.34, 1.61, 1.70 and 1.73% for T01-T04 respectively. Breast muscle represented a significantly higher proportion of body weight at ED18 for all FGF-2 dose groups (T02-T04) compared to controls (T01). MyoD and Glypican-1 genes were up-regulated.

In addition to the advantage of the increase in breast muscle tissue the overall increase in embryo body weights and, more specifically muscle weight, would have a profound implication on viral vaccine manufacturing cost reductions. Increased muscle harvest per embryo would mean increased fibroblast harvest as muscle and fibroblasts are intertwined with each other. More fibroblast per egg would mean fewer eggs required to grow viruses which are grown in fibroblasts for the production of viral vaccines.

This example shows a method of determining increased growth in avians by measuring the levels of transcripts of proteins such as MyoD, Myogenin, Syndecan and Glypican-1 in breast muscle tissues by measuring RNA level of the respective transcripts and comparing against a known housekeeping type gene such as GAPDH.

This example further provides a method of measuring a hyperplastic muscle fibers in ED18 embryos by measuring biomarkers leading to improved vascular supply and thereby no muscle necrosis in market age birds (5 weeks post-hatch).

Example 4

Evaluation of IGF-1 and FGF-2 Administered in Ovo at ED0 and ED4 on Day 33 in Male and Female Cobb 500 Broilers Under Standard Commercial Growth Conditions The objective of this study was to evaluate the impact of standard commercial growth conditions on health the performance of 33-day old male and female broilers that had been administered IGF-1 and FGF-2 in ovo at ED0 or ED4 at three dose levels. Evaluations included weight gain, feed conversion and processing yield.

Standard commercial growth conditions were used which best mimic the conditions under which broilers are typically raised, particularly throughout the southern United States.

TABLE 9

Study Design

| Treatment number | Test Material | Injection Day | Dose Level | No. Birds/Pens | No. Pens M | No. Pens F | No. Birds |
|---|---|---|---|---|---|---|---|
| T01 | Control | None | Control | 18 | 6 | 6 | 216 |
| T02 | FGF | ED0 | 10 ng | 18 | 6 | 6 | 216 |
| T03 | FGF | ED0 | 20 ng | 18 | 6 | 6 | 216 |
| T04 | FGF | ED0 | 40 ng | 18 | 6 | 6 | 216 |
| T05 | FGF | ED4 | 10 ng | 18 | 6 | 6 | 216 |
| T06 | FGF | ED4 | 20 ng | 18 | 6 | 6 | 216 |
| T07 | FGF | ED4 | 40 ng | 18 | 6 | 6 | 216 |
| T08 | IGF | ED0 | 50 ng | 18 | 6 | 6 | 216 |
| T09 | IGF | ED0 | 100 ng | 18 | 6 | 6 | 216 |
| T10 | IGF | ED0 | 200 ng | 18 | 6 | 6 | 216 |
| T11 | IGF | ED4 | 50 ng | 18 | 6 | 6 | 216 |
| T12 | IGF | ED4 | 100 ng | 18 | 6 | 6 | 216 |
| T13 | IGF | ED4 | 200 ng | 18 | 6 | 6 | 216 |
| Totals |  |  |  |  | 78 | 78 | 2808 |

Treatments were administered in ovo on ED0 or ED4 using the following procedure:
1. The air cell of each egg was located by candling and marked in pencil.
2. A hole was punched in the center of the area marked by the circle using an 18 G needle.

3. The assigned treatment was administered a 100 μL volume by dropping into the punched hole using an 18 G ¼" needle inserted to the hub or a Gilman pipette with a plastic pipette tip.
4. The punched hole was sealed with hot glue from a glue gun.
5. Eggs were returned to the incubator.

In this study, during the hatcher phase, treatments were assigned to incubator trays and column according to a completely randomized design with a one-way treatment structure.

On the day of hatch (Day 0), chicks were sexed and allocated to pens and treatments for the grow-out phase according to a split-plot design, with sex as the whole plot factor, and treatment as the sub-plot factor. The whole plot design was a completely randomized design with one-way treatment structure. A total of 10 birds were selected from each pen for processing. Within treatment group and sex, birds were randomly assigned to the pens assigned to that group using the procedures in place. Chicks were placed after vaccination (Newcastle and Infectious Bronchitis vaccines was administered using a spray cabinet) on Day 1. Bird density, temperature, lighting, feeder and water space were similar for all treatment groups.

All birds received a single common starter, grower, and finisher basal feed diet. Feed was provided ad libitum throughout the study (until approximately 12 hrs before scheduled processing time). All birds received a single common Starter, Grower and Finisher basal feed diet. Feed added and removed from pens from Day 1 to study end was weighed and recorded. Water was provided ad libitum throughout the study.

On Day 7 all pens for all treatments were adjusted. Total number of birds to be included in each pen was determined based on the highest number of healthy birds available in all treatments and all pens (obvious culls or sick birds were removed if possible). All birds removed were weighed and recorded on the mortality sheet for each pen.

Birds were weighed, by pen, on approximately Days 1, 7, 14, 21, 28, and Study End (Day 33). The feed remaining in each pen was weighed and recorded on approximately Day 7, 14, 21, 28 and Study End (Day 33). The feed intake during Days 1-7, 1-14, 1-21, 1-28, and 1-33 were calculated. Feed was changed from starter to grower on Day 14, and from grower to finisher on Day 28.

Average bird weight, on a pen basis, on each weigh day was summarized. The average feed conversion was calculated for each measurement period using the total feed consumption for the pen divided by the total weight of surviving birds. Adjusted feed conversion was calculated using the total feed consumption in a pen divided by the total weight of surviving birds and weight of birds that died or were removed from that pen.

On Day 33, approximately 1,560 birds (10 random birds/pen determined by the randomization plan) were individually tagged and processed over the course of two days following the final weights. Birds were processed, as per standard industry procedure, and the breast meat and the leg quarters were removed, weighed and recorded. Two leg quarters on each bird processed were collected. Processing data collected on individual birds included live weight, hot carcass weight, breast weight, superficial pectoral weight, tenders (deep pectoral) weight and leg quarter weight.

The primary variables for analysis were breast weight, average daily gain and feed conversion. Day 33 body weights and carcass data (hot carcass weight, breast weight) were statistically analyzed using mixed linear models. The models contained fixed effects for sex, treatment, and sex by treatment interaction. The random effects included block within sex, block by treatment interaction within sex (pen term), and error. Feed intake (Days 1-33), feed conversion (Days 1-33) and average daily gain (Days 1-33) were analyzed using a mixed linear model. The model contained fixed effects for sex, treatment, and sex by treatment interaction. The random effects included block within sex, and error. Least squares means were used as estimates of treatment means. Standard errors of least squares means were estimated and 90% confidence intervals were constructed. Treatment differences were assessed at the 10% level of significance (P<0.10).

Six pens per treatment group was expected provide at least 88% power to demonstrate a 4% improvement in breast weight; at least 90% power to demonstrate 4% improvement in feed conversion; at least 90% power for 4% improvement in average daily gain for treated over untreated groups at the 0.10 level of significance.

Results

Bird health-mortality was within expected ranges for commercial broiler production. No unusual effects were observed.

The analysis of deep pectoral muscle weight is presented in Table 10. The analysis of total breast weight (superficial plus deep pectoral muscles) is presented in Table 11. The analysis of leg quarter weight is presented in Table 12.

TABLE 10

Analysis of Deep Pectoral Muscle Weight (kg)

| Sex | Treatment | number of birds | LS mean | Std. error | 90% confidence limits | Range | % Δ from T01 | Control Vs Trt. p-value | Significant at 0.10 level |
|---|---|---|---|---|---|---|---|---|---|
| F | T01 (Control) | 60 | 0.045 | 0.0013 | (0.043, 0.047) | 0.031 to 0.062 | | | |
| F | T02 (FGF 10 ng ED0) | 60 | 0.047 | 0.0013 | (0.045, 0.05) | 0.03 to 0.069 | 5.9 | 0.0412 | * |
| F | T03 (FGF 20 ng ED0) | 60 | 0.047 | 0.0013 | (0.044, 0.049) | 0.029 to 0.064 | 3.8 | 0.1857 | ns |
| F | T04 (FGF 40 ng ED0) | 60 | 0.047 | 0.0013 | (0.045, 0.049) | 0.032 to 0.062 | 5.1 | 0.0785 | * |
| F | T05 (FGF 10 ng ED4) | 60 | 0.046 | 0.0013 | (0.044, 0.048) | 0.033 to 0.063 | 2.7 | 0.3548 | ns |
| F | T06 (FGF 20 ng ED4) | 60 | 0.045 | 0.0013 | (0.043, 0.047) | 0.026 to 0.06 | 0.8 | 0.7773 | ns |
| F | T07 (FGF 40 ng ED4) | 60 | 0.046 | 0.0013 | (0.044, 0.048) | 0.031 to 0.06 | 2.4 | 0.4107 | Ns |

TABLE 10-continued

Analysis of Deep Pectoral Muscle Weight (kg)

| Sex | Treatment | number of birds | LS mean | Std. error | 90% confidence limits | Range | % Δ from T01 | Control Vs Trt. p-value | Significant at 0.10 level |
|---|---|---|---|---|---|---|---|---|---|
| F | T08 (IGF 50 ng ED0) | 60 | 0.046 | 0.0013 | (0.044, 0.048) | 0.031 to 0.062 | 2.2 | 0.4560 | ns |
| F | T09 (IGF 100 ng ED0) | 60 | 0.045 | 0.0013 | (0.043, 0.047) | 0.014 to 0.062 | −0.0 | 1.0000 | ns |
| F | T10 (IGF 200 ng ED0) | 60 | 0.047 | 0.0013 | (0.045, 0.05) | 0.033 to 0.059 | 5.9 | 0.0425 | * |
| F | T11 (IGF 50 ng ED4) | 60 | 0.046 | 0.0013 | (0.044, 0.048) | 0.024 to 0.064 | 2.3 | 0.4330 | ns |
| F | T12 (IGF 100 ng ED4) | 60 | 0.048 | 0.0013 | (0.046, 0.05) | 0.033 to 0.089 | 6.5 | 0.0247 | * |
| F | T13 (IGF 200 ng ED4) | 60 | 0.045 | 0.0013 | (0.043, 0.048) | 0.029 to 0.081 | 1.1 | 0.6997 | ns |
| M | T01 (Control) | 60 | 0.044 | 0.0014 | (0.042, 0.047) | 0.031 to 0.065 | | | |
| M | T02 (FGF 10 ng ED0) | 60 | 0.046 | 0.0014 | (0.044, 0.048) | 0.032 to 0.066 | 4.0 | 0.2240 | ns |
| M | T03 (FGF 20 ng ED0) | 60 | 0.045 | 0.0014 | (0.043, 0.047) | 0.032 to 0.066 | 1.7 | 0.6136 | ns |
| M | T04 (FGF 40 ng ED0) | 60 | 0.045 | 0.0014 | (0.043, 0.047) | 0.024 to 0.066 | 1.7 | 0.6136 | ns |
| M | T05 (FGF 10 ng ED4) | 60 | 0.047 | 0.0014 | (0.045, 0.049) | 0.029 to 0.066 | 5.8 | 0.0756 | * |
| M | T06 (FGF 20 ng ED4) | 60 | 0.047 | 0.0014 | (0.044, 0.049) | 0.032 to 0.066 | 5.4 | 0.1011 | ns |
| M | T07 (FGF 40 ng ED4) | 60 | 0.045 | 0.0014 | (0.043, 0.048) | 0.025 to 0.059 | 2.1 | 0.5205 | ns |
| M | T08 (IGF 50 ng ED0) | 60 | 0.047 | 0.0014 | (0.045, 0.05) | 0.028 to 0.068 | 6.8 | 0.0370 | * |
| M | T09 (IGF 100 ng ED0) | 60 | 0.047 | 0.0014 | (0.045, 0.049) | 0.029 to 0.067 | 6.2 | 0.0586 | * |
| M | T10 (IGF 200 ng ED0) | 60 | 0.045 | 0.0014 | (0.043, 0.048) | 0.026 to 0.062 | 2.4 | 0.4558 | ns |
| M | T11 (IGF 50 ng ED4) | 60 | 0.046 | 0.0014 | (0.043, 0.048) | 0.026 to 0.068 | 2.6 | 0.4353 | ns |
| M | T12 (IGF 100 ng ED4) | 60 | 0.045 | 0.0014 | (0.043, 0.048) | 0.024 to 0.067 | 2.5 | 0.4421 | ns |
| M | T13 (IGF 200 ng ED4) | 60 | 0.046 | 0.0014 | (0.044, 0.049) | 0.021 to 0.069 | 4.5 | 0.1723 | ns |

* Statistically significant

Note:
P < 0.10

TABLE 11

Analysis of Total Breast Weight (kg)

| Sex | Treatment | number of birds | LS mean | Std. error | 90% confidence limits | Range | % Δ from T01 | Control Vs Trt. p-value | Significant at 0.10 level |
|---|---|---|---|---|---|---|---|---|---|
| F | T01 (Control) | 60 | 0.255 | 0.0061 | (0.245, 0.265) | 0.15 to 0.335 | | | |
| F | T02 (FGF 10 ng ED0) | 60 | 0.266 | 0.0065 | (0.255, 0.277) | 0.176 to 0.375 | 4.5 | 0.0848 | * |
| F | T03 (FGF 20 ng ED0) | 60 | 0.256 | 0.0071 | (0.244, 0.268) | 0.155 to 0.355 | 0.4 | 0.8825 | ns |
| F | T04 (FGF 40 ng ED0) | 60 | 0.261 | 0.0060 | (0.251, 0.271) | 0.189 to 0.323 | 2.4 | 0.3046 | ns |
| F | T05 (FGF 10 ng ED4) | 60 | 0.253 | 0.0063 | (0.242, 0.264) | 0.179 to 0.338 | −0.8 | 0.7464 | ns |
| F | T06 (FGF 20 ng ED4) | 60 | 0.249 | 0.0066 | (0.238, 0.261) | 0.139 to 0.335 | −2.2 | 0.4132 | ns |
| F | T07 (FGF 40 ng ED4) | 60 | 0.257 | 0.0063 | (0.247, 0.268) | 0.18 to 0.329 | 1.0 | 0.6886 | ns |
| F | T08 (IGF 50 ng ED0) | 60 | 0.256 | 0.0064 | (0.246, 0.267) | 0.147 to 0.334 | 0.6 | 0.8012 | ns |
| F | T09 (IGF 100 ng ED0) | 60 | 0.251 | 0.0062 | (0.241, 0.262) | 0.166 to 0.338 | −1.4 | 0.5576 | ns |

TABLE 11-continued

Analysis of Total Breast Weight (kg)

| Sex | Treatment | number of birds | LS mean | Std. error | 90% confidence limits | Range | % Δ from T01 | Control Vs Trt. p-value | Significant at 0.10 level |
|---|---|---|---|---|---|---|---|---|---|
| F | T10 (IGF 200 ng ED0) | 60 | 0.264 | 0.0059 | (0.254, 0.274) | 0.193 to 0.344 | 3.5 | 0.1429 | ns |
| F | T11 (IGF 50 ng ED4) | 60 | 0.252 | 0.0072 | (0.24, 0.264) | 0.131 to 0.328 | −1.0 | 0.7209 | ns |
| F | T12 (IGF 100 ng ED4) | 60 | 0.260 | 0.0064 | (0.25, 0.271) | 0.17 to 0.337 | 2.2 | 0.3848 | ns |
| F | T13 (IGF 200 ng ED4) | 60 | 0.247 | 0.0063 | (0.236, 0.257) | 0.142 to 0.317 | −3.2 | 0.1987 | ns |
| M | T01 (Control) | 60 | 0.251 | 0.0078 | (0.238, 0.264) | 0.147 to 0.363 | | | |
| M | T02 (FGF 10 ng ED0) | 60 | 0.262 | 0.0070 | (0.251, 0.274) | 0.163 to 0.357 | 4.5 | 0.1875 | ns |
| M | T03 (FGF 20 ng ED0) | 60 | 0.256 | 0.0068 | (0.244, 0.267) | 0.178 to 0.359 | 1.9 | 0.5693 | ns |
| M | T04 (FGF 40 ng ED0) | 60 | 0.257 | 0.0077 | (0.244, 0.27) | 0.142 to 0.38 | 2.5 | 0.5013 | ns |
| M | T05 (FGF 10 ng ED4) | 60 | 0.275 | 0.0176 | (0.245, 0.304) | 0.165 to 1.218 | 9.4 | 0.2005 | ns |
| M | T06 (FGF 20 ng ED4) | 60 | 0.264 | 0.0066 | (0.252, 0.275) | 0.185 to 0.372 | 5.0 | 0.1258 | ns |
| M | T07 (FGF 40 ng ED4) | 60 | 0.256 | 0.0073 | (0.244, 0.269) | 0.125 to 0.339 | 2.2 | 0.5326 | ns |
| M | T08 (IGF 50 ng ED0) | 60 | 0.268 | 0.0074 | (0.256, 0.28) | 0.158 to 0.362 | 6.8 | 0.0568 | * |
| M | T09 (IGF 100 ng ED0) | 60 | 0.264 | 0.0070 | (0.252, 0.276) | 0.172 to 0.378 | 5.2 | 0.1283 | ns |
| M | T10 (IGF 200 ng ED0) | 60 | 0.261 | 0.0078 | (0.248, 0.274) | 0.126 to 0.37 | 4.1 | 0.2647 | ns |
| M | T11 (IGF 50 ng ED4) | 60 | 0.259 | 0.0073 | (0.247, 0.271) | 0.154 to 0.355 | 3.3 | 0.3401 | ns |
| M | T12 (IGF 100 ng ED4) | 60 | 0.258 | 0.0072 | (0.246, 0.27) | 0.132 to 0.349 | 2.8 | 0.4197 | ns |
| M | T13 (IGF 200 ng ED4) | 60 | 0.260 | 0.0077 | (0.247, 0.272) | 0.125 to 0.378 | 3.4 | 0.3483 | ns |

* Statistically significant

Note:
P < 0.10

TABLE 12

Analysis of Leg Quarter Weight (kg)

| Sex | Treatment | number of animals | LS mean | Std. error | 90% confidence limits | Range | % Δ from T01 | Control Vs Trt. p-value | Significant at 0.10 level |
|---|---|---|---|---|---|---|---|---|---|
| F | T01 (Control) | 60 | 0.295 | 0.0061 | (0.285, 0.306) | 0.187 to 0.352 | | | |
| F | T02 (FGF 10 ng ED0) | 60 | 0.295 | 0.0061 | (0.285, 0.305) | 0.222 to 0.392 | −0.2 | 0.9313 | ns |
| F | T03 (FGF 20 ng ED0) | 60 | 0.292 | 0.0061 | (0.282, 0.302) | 0.205 to 0.354 | −1.2 | 0.5381 | ns |
| F | T04 (FGF 40 ng ED0) | 60 | 0.301 | 0.0061 | (0.29, 0.311) | 0.227 to 0.373 | 1.8 | 0.3504 | ns |
| F | T05 (FGF 10 ng ED4) | 60 | 0.286 | 0.0061 | (0.275, 0.296) | 0.224 to 0.352 | −3.2 | 0.0886 | * |
| F | T06 (FGF 20 ng ED4) | 60 | 0.290 | 0.0061 | (0.28, 0.3) | 0.206 to 0.359 | −1.8 | 0.3353 | ns |
| F | T07 (FGF 40 ng ED4) | 60 | 0.293 | 0.0061 | (0.283, 0.304) | 0.209 to 0.368 | −0.8 | 0.6902 | ns |
| F | T08 (IGF 50 ng ED0) | 60 | 0.292 | 0.0061 | (0.281, 0.302) | 0.216 to 0.364 | −1.3 | 0.5034 | ns |
| F | T09 (IGF 100 ng ED0) | 60 | 0.286 | 0.0061 | (0.276, 0.297) | 0.201 to 0.389 | −3.1 | 0.1053 | ns |
| F | T10 (IGF 200 ng ED0) | 60 | 0.295 | 0.0061 | (0.284, 0.305) | 0.248 to 0.38 | −0.2 | 0.8959 | ns |
| F | T11 (IGF 50 ng ED4) | 60 | 0.293 | 0.0061 | (0.283, 0.304) | 0.2 to 0.358 | −0.7 | 0.7234 | ns |

TABLE 12-continued

Analysis of Leg Quarter Weight (kg)

| Sex | Treatment | number of animals | LS mean | Std. error | 90% confidence limits | Range | % Δ from T01 | Control Vs Trt. p-value | Significant at 0.10 level |
|---|---|---|---|---|---|---|---|---|---|
| F | T12 (IGF 100 ng ED4) | 60 | 0.295 | 0.0061 | (0.285, 0.305) | 0.214 to 0.356 | −0.2 | 0.9265 | ns |
| F | T13 (IGF 200 ng ED4) | 60 | 0.291 | 0.0061 | (0.28, 0.301) | 0.217 to 0.38 | −1.6 | 0.4067 | ns |
| M | T01 (Control) | 60 | 0.314 | 0.0071 | (0.302, 0.326) | 0.235 to 0.404 | | | |
| M | T02 (FGF 10 ng ED0) | 60 | 0.328 | 0.0071 | (0.316, 0.339) | 0.227 to 0.409 | 4.4 | 0.0678 | * |
| M | T03 (FGF 20 ng ED0) | 60 | 0.325 | 0.0071 | (0.313, 0.337) | 0.248 to 0.403 | 3.5 | 0.1435 | ns |
| M | T04 (FGF 40 ng ED0) | 60 | 0.328 | 0.0071 | (0.316, 0.34) | 0.213 to 0.44 | 4.6 | 0.0582 | * |
| M | T05 (FGF 10 ng ED4) | 60 | 0.329 | 0.0071 | (0.317, 0.341) | 0.248 to 0.426 | 4.9 | 0.0444 | * |
| M | T06 (FGF 20 ng ED4) | 60 | 0.334 | 0.0071 | (0.322, 0.346) | 0.234 to 0.415 | 6.5 | 0.0073 | * |
| M | T07 (FGF 40 ng ED4) | 60 | 0.319 | 0.0071 | (0.307, 0.331) | 0.18 to 0.431 | 1.8 | 0.4543 | ns |
| M | T08 (IGF 50 ng ED0) | 60 | 0.335 | 0.0071 | (0.323, 0.347) | 0.251 to 0.407 | 6.8 | 0.0048 | * |
| M | T09 (IGF 100 ng ED0) | 60 | 0.331 | 0.0071 | (0.319, 0.343) | 0.255 to 0.423 | 5.6 | 0.0215 | * |
| M | T10 (IGF 200 ng ED0) | 60 | 0.326 | 0.0071 | (0.314, 0.337) | 0.197 to 0.405 | 3.8 | 0.1169 | ns |
| M | T11 (IGF 50 ng ED4) | 60 | 0.319 | 0.0071 | (0.308, 0.331) | 0.22 to 0.393 | 1.8 | 0.4464 | ns |
| M | T12 (IGF 100 ng ED4) | 60 | 0.327 | 0.0071 | (0.315, 0.339) | 0.198 to 0.408 | 4.2 | 0.0864 | * |
| M | T13 (IGF 200 ng ED4) | 60 | 0.323 | 0.0071 | (0.311, 0.335) | 0.188 to 0.437 | 3.1 | 0.2072 | ns |

\* Statistically significant

Note:

$P < 0.10$

In female birds, administration of FGF-2 at 10 ng on ED0 resulted in significant increases in total breast muscle (4.5%) and in deep breast muscle (5.9%). Significant increases in deep muscle breast were also observed in female birds after administration of FGF-2 at 40 ng (5.1%) on ED0, IGF-1 at 200 ng on ED0 (5.9%) and IGF-1 at 100 ng) on ED4 (6.5%).

In male birds, IGF-1 administered at 50 ng on ED0 resulted in a significant increase in total breast muscle weight, deep muscle weight and leg quarter weight (6.8% increase for each). Significant increases in deep breast muscle (5.8%) and leg quarter (4.9%) were also observed in male birds after administration of FGF-2 at 10 ng on ED4. Administration of 100 ng IGF-1 to male birds on ED0 resulted in significant increases in deep breast muscle (6.2%) and leg quarter weight (5.6%). Significant increases in leg quarter weight in males were also observed after administration of FGF-2 at 10 ng on ED0 (4.4%), FGF-2 at 40 ng on ED0 (4.6%), FGF-2 at 20 ng on ED4 (6.5%), IGF-1 at 100 ng on ED0 (5.6%) and IGF-1 at 100 ng on ED4 (4.2%).

In conclusion, the overall body weights for the sexes combined had numerically positive percentage changes compared to the controls. The administration of FGF-2 at 10 ng and ED0 and IGF-1 at 50 ng produced the highest increase in muscle mass over controls.

Additionally, an increase in the leg muscles in synchronization with the increase in breast muscle results in a sturdier and a healthier bird free of ambulatory problems. This also allows bulkier birds get around to the feeders to obtain feed thereby preventing diseases and starvation. In this way the larger birds have a significant health benefit.

An additional advantage regarding the increase in muscle is that the birds will reach target industry muscle weights sooner than 5 weeks, for example reaching target industry muscle weight by 4 week, thus resulting in huge savings in labor housing, feed and water.

Example 5

Evaluation of IGF-1 or FGF-2 Administered in Ovo at ED18 on Male and Female Cobb 500 Broilers at Grow-Out

TABLE 13

Study Design

| Treatment Number | Test Material | Injection Day | Dose Level | No. Birds/ Pens | No. Pens M | No. Pens F | No. Birds |
|---|---|---|---|---|---|---|---|
| T01 | Control | None | PBS Injected Control | 19 | 20 | 20 | 760 |
| T02 | FGF-1 | ED18 | Low | 19 | 20 | 20 | 760 |
| T03 | FGF-1 | ED18 | High | 19 | 20 | 20 | 760 |
| T04 | IGF-2 | ED18 | Low | 19 | 20 | 20 | 760 |
| T05 | IGF-2 | ED18 | High | 19 | 20 | 20 | 760 |

Treatments according to Table 13 will be administered in ovo on ED18 using the following procedure:

1. The appropriate structure, preferably the amnion for ED18, to inject of each egg will be located.

2. A hole will be punched in the center of the area marked
3. The assigned treatment will be administered in about a 100 μL, although volume could vary, by dropping into the punched hole.
4. The punched hole will be sealed with hot glue from a glue gun.
5. Eggs will be returned to the incubator.

The in ovo injection could be performed manually or by using a device that can pierce the egg shell and deliver the treatment substance to the interior of the egg.

Birds will be housed within an environmentally-controlled facility in concrete floor pens, with used litter as bedding. Birds will not receive Mareks vaccinations at the hatchery. Newcastle and Infectious Bronchitis (NCB) vaccine will be administered using a spray cabinet, upon receipt of chicks. No other vaccinations or treatments (except as indicated in Table 13) will be administered during the study.

Water and feed will be provided ad libitum throughout the study. A chick feeder tray will be placed in each pen for approximately the first 4 days. All birds will receive a single common Starter, Grower, and Finisher basal feed diet. They will be placed on a single common Starter basal feed diet upon receipt (Day 0). All diet changes will be conducted at the same time for all pens. Feed added and removed from pens from Day 0 to study end will be weighed and recorded. The test facility, pens and birds will be observed at least twice daily for general flock condition, lighting, water, feed, ventilation and unanticipated events. If abnormal conditions or abnormal behavior is noted at any of the twice-daily observations, they will be documented.

Birds and feed remaining in each pen will be weighed and recorded by pen on a weekly basis starting on day 7. The feed intake for each pen will be determined at each body weight measurement period by taking the amount of feed weighed into the pen, minus the amount of feed remaining in the feeder when birds are weighed. Average bird weight, on a pen basis, on each weigh day will be summarized. The average feed conversion will be calculated for each measurement period, using the total feed consumption for the pen divided by the total weight of surviving birds. Adjusted feed conversion will be calculated using the total feed consumption in a pen, divided by the total weight of surviving birds and weight of birds that died or were removed from that pen.

Selected trays and stacks of hatcher will be allocated to treatments according to a randomization plan. Treatments will be assigned to hatcher trays and stacks according to a completely randomized design with one-way treatment structure. Each treatment will be assigned to 10 trays containing 130 eggs each, for a total of 1300 eggs per treatment. The experimental unit for treatment at this phase of the study is tray by stack combination.

During the grow-out phase, chicks will be allocated to treatments and pens according to a randomization plan. On the day of hatching (day 0), chicks will be sexed and allocated to pens and treatments according to a split-plot design, with sex as the whole plot factor, and treatment as the sub-plot factor. Blocks will be randomly assigned to day of necropsy so as to preserve balance for sex and treatment within day of necropsy.

The primary variables for analysis will be breast weight, average daily gain and feed conversion. Carcass data (end live weight, hot carcass weight, carcass components, and ratio of components to hot carcass weight) will be analyzed using mixed linear models. The models will contain fixed effects for sex, treatment, day of necropsy, and all interactions among those effects. The random effects will include block, the block by sex interaction, the block by treatment interaction, the block by sex by treatment interaction (pen term), and residual.

Body weight will be analyzed using a mixed linear model for repeated measures. The model will include fixed effects for sex, treatment and day of study and all interactions among those effects. The random effects will include block, the block by sex interaction, the block by treatment interaction, the block by sex by treatment interaction, and residual. Average daily gain for study period and weekly periods will be estimated for each treatment group using the statistical model for bodyweight.

Feed intake (days 0-35), feed conversion (days 0-35) will be analyzed using a mixed linear model. The model will contain fixed effects for sex, treatment, and sex by treatment interaction. The random effects will include block, the block by sex interaction, the block by treatment interaction, the block by sex by treatment interaction, and residual.

Least squares means will be used as estimates of treatment means for the above models. Standard errors of least squares means will be estimated and 90% confidence intervals will be constructed. A priori contrasts will be used to assess treatment differences provided that at least one of the treatment related effects is significant. Comparisons of interest will include T01 vs all other treatments (within time point for repeated measures models, and within sex, if there are significant sex related treatment effects). Treatment differences will be assessed at the 10% level of significance ($P<0.10$).

Birds will be euthanized and will be weighed and recorded. The breast meat and the leg quarters will be removed, weighed and recorded. Processing data will be collected on individual birds, including live weight, hot carcass weight, hot boneless, skinless breast; superficial pectoral and tenders (deep pectoral) and hot leg quarter weight.

Example 6

Effect of Chicken Fibroblast Growth Factor Administered in Ovo on ED18 Embryo Breast Muscle Weight This study was designed to investigate the effect of chicken fibroblast growth factor (cFGF: SEQ ID NO. 3) on E18 breast muscle weights as compared to hFGF-2. This study compares high and low doses of cFGF and human FGF (hFGF2) administered in ovo at ED0 versus controls. The dosing method is in ovo directly on the air cell on ED0.

Vehicle control comprises 20 mM Citrate buffer pH 6+Sucrose+EDTA+Methionine+Tween-80. Both Cobb and Ross breed eggs were used in this study.

Study Setup

| Egg breed | Treatment | Dose per egg | Volume per egg | Number of eggs |
|---|---|---|---|---|
| Ross 308 | T01 Uninjected | — | 50 μl | 60 |
| Ross 308 | T02 Vehicle | — | 50 μl | 60 |
| Ross 308 | T03 cFGF | 10 ng | 50 μl | 60 |
| Ross 308 | T04 cFGF | 30 ng | 50 μl | 60 |
| Ross 308 | T05 hFGF | 10 ng | 50 μl | 60 |
| Cobb 500 | T06 Uninjected | — | 50 μl | 60 |
| Cobb 500 | T07 Vehicle | — | 50 μl | 60 |
| Cobb 500 | T08 cFGF | 10 ng | 50 μl | 60 |
| Cobb 500 | T09 cFGF | 30 ng | 50 μl | 60 |
| Cobb 500 | T10 hFGF | 10 ng | 50 μl | 60 |

On ED18, all viable eggs from each control and treated groups were euthanized and *P. major* breast muscle was extracted and weighed. Muscle was collected for histology and RNA extraction for muscle gene biomarkers.

Data was analyzed as follows: breast weight was analyzed using a mixed linear model. The models contained fixed effects for treatment, and the random effect for residual error.

Least squares means were used as estimates of treatment means. Standard errors of least squares means were estimated and 90% confidence intervals and constructed. A priori contrasts were used to assess treatment differences using Fisher's protected LSD provided that the treatment effect is significant. Treatment differences were assessed at the 10% level of significance (P<0.10).

Results:

| Egg breed | Treatment | Number of birds | LS mean | Std. error | % Δ from T01 | % Δ from T02 | Control T01 Vs Trt. p-value | Significant at 0.10 level | Control T02 Vs Trt. p-value | Significant at 0.10 level |
|---|---|---|---|---|---|---|---|---|---|---|
| Ross 308 | T01 Uninjected | 40 | 0.491 | 0.0096 | — | NA | — | — | | |
| Ross 308 | T02 Vehicle | 40 | 0.513 | 0.0114 | NA | — | — | — | | |
| Ross 308 | T03 cFGF 10 ng | 40 | 0.496 | 0.0119 | 0.85 | −3.39 | 0.7846 | NO | 0.2943 | NO |
| Ross 308 | T04 cFGF 30 ng | 40 | 0.567 | 0.0152 | 15.4 | 10.54 | 0.0001 | YES | 0.0058 | YES |
| Ross 308 | T05 hFGF 10 ng | 40 | 0.537 | 0.0101 | 9.34 | 4.74 | 0.0015 | YES | 0.1145 | NO |
| Cobb 500 | T06 Uninjected | 40 | 0.47 | 0.0113 | — | NA | — | — | NA | |
| Cobb 500 | T07 Vehicle | 40 | 0.451 | 0.0096 | NA | — | NA | — | | |
| Cobb 500 | T08 cFGF 10 ng | 40 | 0.517 | 0.0126 | 10.15 | 14.63 | 0.006 | YES | <0.0001 | YES |
| Cobb 500 | T09 cFGF 30 ng | 40 | 0.548 | 0.0091 | 16.75 | 21.5 | <0.0001 | YES | <0.0001 | YES |
| Cobb 500 | T10 hFGF 10 ng | 40 | 0.547 | 0.0137 | 16.49 | 21.23 | <0.0001 | YES | <0.0001 | YES |

Summary:

This study showed that the Cobb and Ross strains of birds both showed significant increases in breast muscle at embryonal day 18 with the chicken FGF. A dose related effect was noted.

Example 7

Effect of Chicken FGF-2 Given in Ovo on 35 Day Broiler Bird Breast Muscle Weight This study was designed to investigate the effect of chicken fibroblast growth factor (cFGF: SEQ ID NO. 3) on breast muscle weights of mature market age birds (breed Cobb 500). This study compares high and low doses administered in ovo at ED0 in the egg air cell.

Study Design

| Treatment Group # | Treatment | Dose | Injection Volume | Number of Eggs |
|---|---|---|---|---|
| T01 | Uninjected Control | N/A | 50 ul | 200 |
| T02 | Low Dose | 30 ng | 50 ul | 200 |
| T03 | High Dose | 60 ng | 50 ul | 200 |
| Total | | | | 600 |

Data Collected
  Daily observation of facility and birds, daily facility temperature.
  Individual bird weights on days 0, 7, 14, 21, 28 and 35.
  Processing day: body weight and breast meat wt.
  Mortality: sex, weight and probable cause of death.
  Removed birds: reason for culling, sex and weight.
  All removals and mortalities were weighed and necropsied for cause of death and sex was determined.

Data Analysis:

The primary variables for analysis were breast weight and average daily gain. Secondary variables for analysis included carcass weight, ratio of carcass weight to live weight and ratio of breast weight to carcass weight.

Body weight was analyzed using a mixed linear model for repeated measures. The model included the fixed effects for treatment, day of study and the treatment by day of study interaction. The random effects included animal within treatment and residual error.

Treatment least squares means for body weight and average daily gain for study periods (0-14, 28-34, and 0-34) were estimated from the repeated measures model for body weight.

Standard errors of least squares means were estimated and 90% confidence intervals were constructed.

Day 35 body weights and carcass data (breast weight, carcass weight, ratio of breast weight to carcass weight, ratio of carcass weight to live weight) were analyzed using a mixed linear model. The models contain fixed effects for sex, treatment, and sex by treatment interaction, and the random effect for residual error. Least squares means were used as estimates of treatment means. Standard errors of least squares means will be estimated and 90% confidence intervals were constructed.

A priori contrasts will be used to assess treatment differences using Fisher's protected LSD provided that at least one of the treatment related effects is significant. Treatment differences were assessed at the 10% level of significance (P<0.10).

Results:

| Sex | Treatment | Number of birds | LS mean | Std. error | % Δ from T01 | Control Vs Trt. p-value | Significant at 0.10 level |
|---|---|---|---|---|---|---|---|
| F | T01 (Control) | 50 | 345.7 | 6.96 | — | — | — |

-continued

| Sex | Treatment | Number of birds | LS mean | Std. error | % Δ from T01 | Control Vs Trt. p-value | Significant at 0.10 level |
|---|---|---|---|---|---|---|---|
| F | T02 (FGF 30 ng ED0) | 50 | 353.3 | 7.69 | 2.2 | 0.4241 | ns |
| F | T03 (FGF 60 ng ED0) | 50 | 361.7 | 9.16 | 4.6 | 0.1374 | ns |
| M | T01 (Control) | 50 | 368.8 | 12.16 | — | — | — |
| M | T02 (FGF 30 ng ED0) | 50 | 382.1 | 8.25 | 3.6 | 0.35 | ns |
| M | T03 (FGF 60 ng ED0) | 50 | 402.1 | 9.14 | 9 | 0.024 | * |

* Statistically significant
Note:
P < 0.10

Summary:
Breast Muscle Weights:
 In males there was a 9% increase of breast muscle yield over controls and in females this increase was 4.6%. This study confirms results from our previous studies in Cobb strain of birds
Gene Expression Data
 The gene expression for the Cobb Grow out at 35 days of age shows differences in terms of the growth pattern of the muscle from the Ross bird. The Cobb bird has less proliferation of the muscle cells as shown by the MyoD expression. In the males differentiation is high as shown by the high levels of myogenin (MGN). Myogenin is a marker of differentiation. This is less in the female. Certainly the muscle weight increase in the treated groups is supported by these data for myogenin. MRF4 is intriguing as MRF4 is traditionally thought to be expressed for fiber formation only but recent evidence indicates a role in proliferation. In the males the combined data suggested the FGF treatment increased determination at 35 d but fiber formation is not affected. However, in the female the increase in MRF4 with the treatment groups could be suggestive of some mature fiber development.
Muscle Histology
 The results with treatment with these compounds improves the breast morphological structure. Individual fibers become apparent with increased perimysial and endomysial spacing. Endomysial and perimysial spacing is essential in preventing fiber degeneration as is observed in the controls. Capillary beds are located within these connective tissue layers and one function is to remove lactic acid build up from muscle fiber damage. Also these spaces contain connective tissue molecules involved in tissue hydration. The changes observed especially with treatment are a significant improvement which should enhance meat quality. Also the muscle weight yield increase at day 35 is significant and in the males was almost 9%.

The invention claimed is:

1. A method of increasing muscle mass in a chicken, comprising the steps of:
   a) administering a composition comprising between about 10-40 ng of Fibroblast Growth Factor-2; and a pharmaceutically acceptable carrier in ovo to an embryonated chicken egg between embryonal day 0 and embryonal day 4; and
   b) incubating said embryonated chicken egg until hatch; wherein said Fibroblast Growth Factor-2 is selected from SEQ ID NO.1 or SEQ ID NO. 3.

2. The method of claim 1 wherein said administration occurs on about embryonal day 0.

3. The method of claim 1 wherein said administration occurs on about embryonal day 1 (ED1).

4. The method of claim 1 wherein said administration occurs on about embryonal day 2 (ED2).

5. The method of claim 1 wherein said administration occurs on about embryonal day 3 (ED3).

6. The method of claim 1 wherein said administration occurs on about embryonal day 4 (ED4).

* * * * *

SEQUENCE LISTING

```
<160> NUMBER OF SEQ ID NOS: 12

<210> SEQ ID NO 1
<211> LENGTH: 154
<212> TYPE: PRT
<213> ORGANISM: human

<400> SEQUENCE: 1

Ala Ala Gly Ser Ile Thr Thr Leu Pro Ala Leu Pro Glu Asp Gly Gly
1               5                   10                  15

Ser Gly Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Ile Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Asp Glu Cys Phe Phe Glu Arg Leu Glu Ser Asn Asn Tyr Asn
            100                 105                 110

Thr Tyr Arg Ser Arg Lys Tyr Thr Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150

<210> SEQ ID NO 2
<211> LENGTH: 70
<212> TYPE: PRT
```

<213> ORGANISM: Human

<400> SEQUENCE: 2

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 3
<211> LENGTH: 157
<212> TYPE: PRT
<213> ORGANISM: gallus gallus

<400> SEQUENCE: 3

Ala Ala Gly Ala Ala Gly Ser Ile Thr Thr Leu Pro Ala Leu Pro Asp
1               5                   10                  15

Asp Gly Gly Gly Ala Phe Pro Pro Gly His Phe Lys Asp Pro Lys
                20                  25                  30

Arg Leu Tyr Cys Lys Asn Gly Gly Phe Phe Leu Arg Ile Asn Pro Asp
            35                  40                  45

Gly Arg Val Asp Gly Val Arg Glu Lys Ser Asp Pro His Ile Lys Leu
    50                  55                  60

Gln Leu Gln Ala Glu Glu Arg Gly Val Val Ser Ile Lys Gly Val Ser
65                  70                  75                  80

Ala Asn Arg Phe Leu Ala Met Lys Glu Asp Gly Arg Leu Leu Ala Leu
                85                  90                  95

Lys Cys Ala Thr Glu Glu Cys Phe Phe Phe Glu Arg Leu Glu Ser Asn
            100                 105                 110

Asn Tyr Asn Thr Tyr Arg Ser Arg Lys Tyr Ser Asp Trp Tyr Val Ala
        115                 120                 125

Leu Lys Arg Thr Gly Gln Tyr Lys Pro Gly Pro Lys Thr Gly Pro Gly
    130                 135                 140

Gln Lys Ala Ile Leu Phe Leu Pro Met Ser Ala Lys Ser
145                 150                 155

<210> SEQ ID NO 4
<211> LENGTH: 70
<212> TYPE: PRT
<213> ORGANISM: gallus gallus

<400> SEQUENCE: 4

Gly Pro Glu Thr Leu Cys Gly Ala Glu Leu Val Asp Ala Leu Gln Phe
1               5                   10                  15

Val Cys Gly Asp Arg Gly Phe Tyr Phe Ser Lys Pro Thr Gly Tyr Gly
                20                  25                  30

Ser Ser Ser Arg Arg Leu His His Lys Gly Ile Val Asp Glu Cys Cys
            35                  40                  45

Phe Gln Ser Cys Asp Leu Arg Arg Leu Glu Met Tyr Cys Ala Pro Ile
    50                  55                  60

Lys Pro Pro Lys Ser Ala
65                  70

```
<210> SEQ ID NO 5
<211> LENGTH: 20
<212> TYPE: DNA
<213> ORGANISM: ARTIFICIAL
<220> FEATURE:
<223> OTHER INFORMATION: TURKEY MYOD FORWARD PRIMER

<400> SEQUENCE: 5
gatggcatga tggagtacag                                          20

<210> SEQ ID NO 6
<211> LENGTH: 20
<212> TYPE: DNA
<213> ORGANISM: ARTIFICIAL
<220> FEATURE:
<223> OTHER INFORMATION: TURKEY MYOD REVERSE PRIMER

<400> SEQUENCE: 6
agcttcagct ggaggcagta                                          20

<210> SEQ ID NO 7
<211> LENGTH: 21
<212> TYPE: DNA
<213> ORGANISM: ARTIFICIAL
<220> FEATURE:
<223> OTHER INFORMATION: TURKEY MYOGENIN FORWARD PRIMER

<400> SEQUENCE: 7
cctttcccac tcctctccaa a                                        21

<210> SEQ ID NO 8
<211> LENGTH: 21
<212> TYPE: DNA
<213> ORGANISM: ARTIFICIAL
<220> FEATURE:
<223> OTHER INFORMATION: TURKEY MYOGENIN REVERSE PRIMER

<400> SEQUENCE: 8
gaccttggtc gaagagcaac t                                        21

<210> SEQ ID NO 9
<211> LENGTH: 20
<212> TYPE: DNA
<213> ORGANISM: ARTIFICIAL
<220> FEATURE:
<223> OTHER INFORMATION: GLYPICAN1 FORWARD PRIMER

<400> SEQUENCE: 9
acatcgggaa tgatgtggat                                          20

<210> SEQ ID NO 10
<211> LENGTH: 20
<212> TYPE: DNA
<213> ORGANISM: ARTIFICIAL
<220> FEATURE:
<223> OTHER INFORMATION: GLYPICAN 1 REVERSE PRIMER

<400> SEQUENCE: 10
aagaggagga aggcagaagg                                          20

<210> SEQ ID NO 11
<211> LENGTH: 20
<212> TYPE: DNA
<213> ORGANISM: ARTIFICIAL
<220> FEATURE:
```

```
<223> OTHER INFORMATION: SYNDECAN 4 FORWARD PRIMER

<400> SEQUENCE: 11
ccaacagcag catctttgaa                                         20

<210> SEQ ID NO 12
<211> LENGTH: 20
<212> TYPE: DNA
<213> ORGANISM: ARTIFICIAL
<220> FEATURE:
<223> OTHER INFORMATION: SYNDECAN 4 REVERSE PRIMER

<400> SEQUENCE: 12
gatgggtttc ttcccaaggt                                         20
```